US012171551B2

(12) United States Patent
Metzmaker et al.

(10) Patent No.: US 12,171,551 B2
(45) Date of Patent: Dec. 24, 2024

(54) APPLICATORS FOR GLUCOSE MONITORS, METHODS FOR APPLYING GLUCOSE MONITORS, AND GLUCOSE MONITORS FOR USE WITH SUCH APPLICATORS

(71) Applicant: LAXMI THERAPEUTIC DEVICES, INC., Goleta, CA (US)

(72) Inventors: Thomas Metzmaker, Goleta, CA (US); Matthew Yavorsky, Granada Hills, CA (US); Michael I. Larkin, Santa Barbara, CA (US); William Peter Van Antwerp, Santa Clarita, CA (US); Scott Mallett, Coto De Caza, CA (US); Dallin Ostler, Goleta, CA (US)

(73) Assignee: LAXMI THERAPEUTIC DEVICES, INC., Goleta, CA (US)

( * ) Notice: Subject to any disclaimer, the term of this patent is extended or adjusted under 35 U.S.C. 154(b) by 0 days.

(21) Appl. No.: 18/511,833

(22) Filed: Nov. 16, 2023

(65) Prior Publication Data

US 2024/0156376 A1 May 16, 2024

Related U.S. Application Data

(60) Provisional application No. 63/425,975, filed on Nov. 16, 2022.

(51) Int. Cl.
*A61B 5/145* (2006.01)
*A61B 90/00* (2016.01)

(52) U.S. Cl.
CPC .......... *A61B 5/14532* (2013.01); *A61B 90/08* (2016.02); *A61B 2560/04* (2013.01); *A61B 2562/02* (2013.01)

(58) Field of Classification Search
CPC . A61B 2560/04; A61B 2562/02; A61B 5/145; A61B 5/14503; A61B 5/14507;
(Continued)

(56) References Cited

U.S. PATENT DOCUMENTS

2017/0188912 A1* 7/2017 Halac ................. A61B 5/14532
2017/0290533 A1* 10/2017 Antonio ............. A61M 5/1723
(Continued)

OTHER PUBLICATIONS

International Search Report and Written Opinion for Application No. PCT/US2023/080146, mailed Mar. 15, 2024, 7 pages.

*Primary Examiner* — Eric J Messersmith
(74) *Attorney, Agent, or Firm* — Lewis Roca Rothgerber Christie LLP

(57) ABSTRACT

An applicator assembly for applying at least a portion of an analyte monitor includes a frame having a longitudinal axis and an opening, a resilient member having at least a first portion fixed relative to the frame and a second portion movable axially relative to the frame, a needle, and a cap engageable with the frame to cover at least part of the opening. The cap is adjustable to increase a bias on the resilient member and to move the second portion of the resilient member away from the opening. When the cap is separated from the frame, the second portion of the resilient member is configured to be held relative to the frame. The hold on the second portion of the resilient member is releasable, such that the bias on the resilient member advances the second portion of the resilient member and the needle towards the opening.

20 Claims, 33 Drawing Sheets

(58) Field of Classification Search
CPC .............. A61B 5/1451; A61B 5/14514; A61B
5/14517; A61B 5/14521; A61B 5/14525;
A61B 5/14528; A61B 5/14532; A61B
5/14535; A61B 5/14539; A61B 5/14542;
A61B 5/14546; A61B 90/08
See application file for complete search history.

(56) References Cited

U.S. PATENT DOCUMENTS

| | | | |
|---|---|---|---|
| 2020/0196919 A1 | 6/2020 | Rao et al. | |
| 2020/0359964 A1 | 11/2020 | Antonio et al. | |
| 2021/0282674 A1 | 9/2021 | Halac et al. | |
| 2021/0290117 A1 | 9/2021 | Chae et al. | |
| 2022/0047188 A1* | 2/2022 | Wehowski | A61B 5/0031 |
| 2022/0202448 A1* | 6/2022 | Shah | A61B 5/0004 |
| 2023/0200852 A1* | 6/2023 | Wiegand | A61B 5/6849 |
| | | | 600/309 |
| 2023/0225728 A1* | 7/2023 | List | A61B 5/14503 |
| | | | 227/175.1 |
| 2024/0075210 A1* | 3/2024 | Garai | A61B 5/6801 |

\* cited by examiner

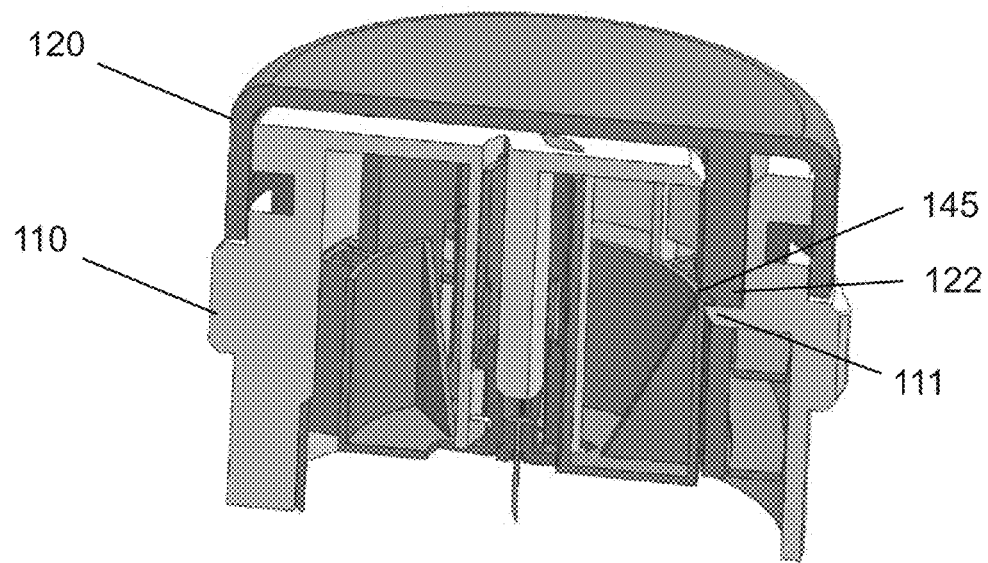
FIG. 13A
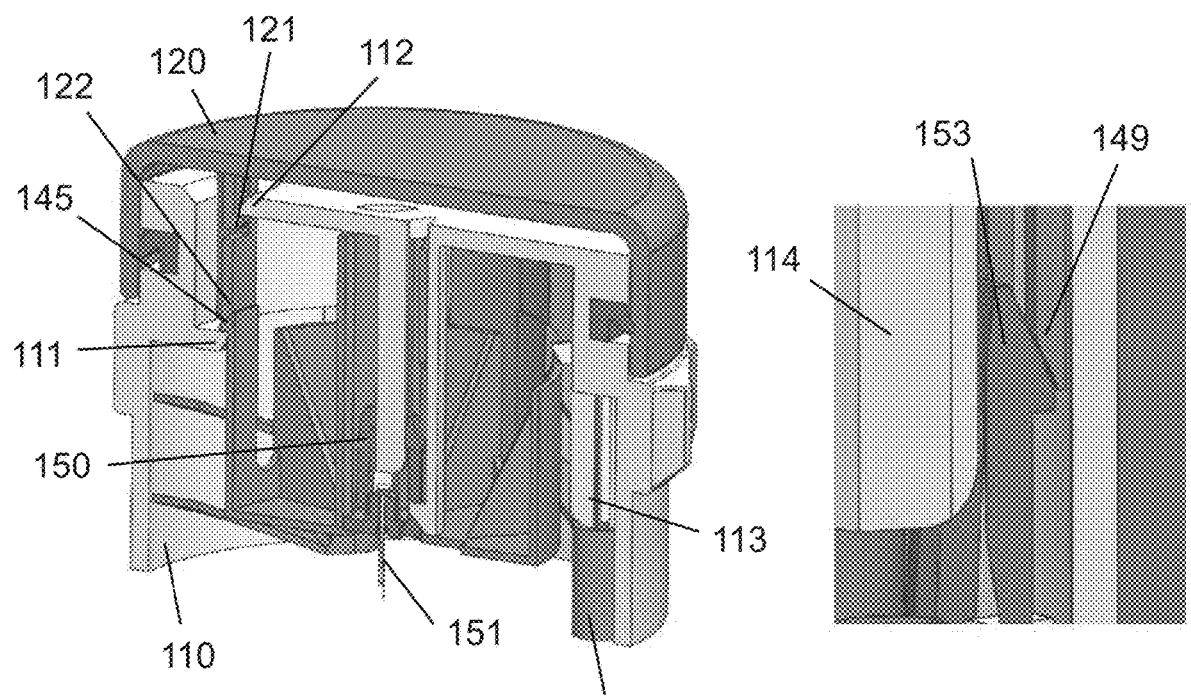
FIG. 13B  FIG. 13C

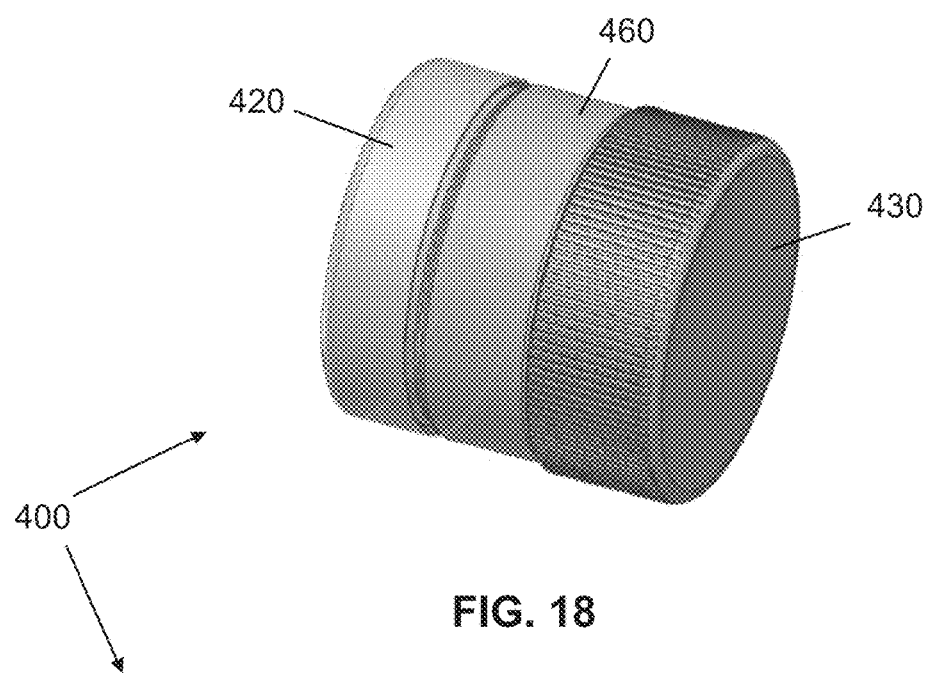
FIG. 18
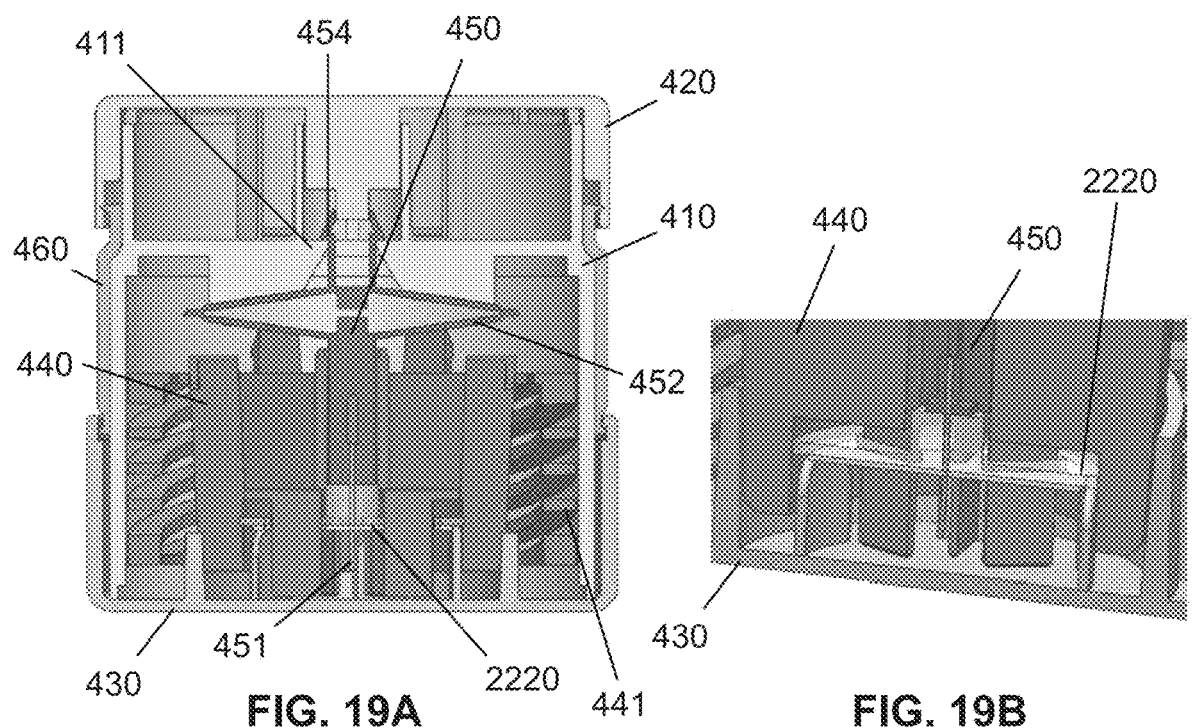
FIG. 19A  FIG. 19B

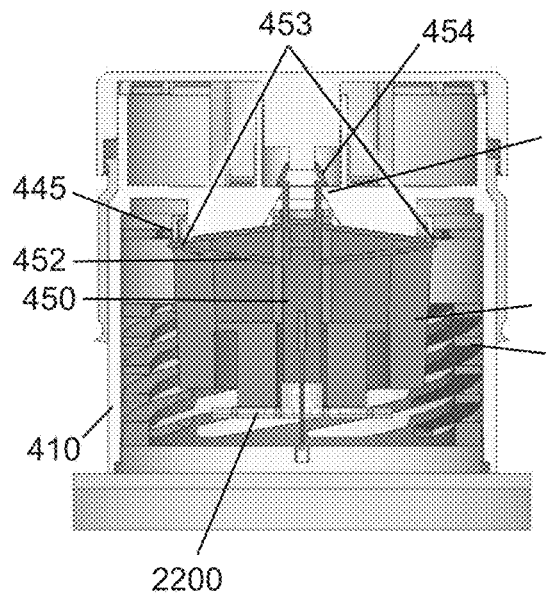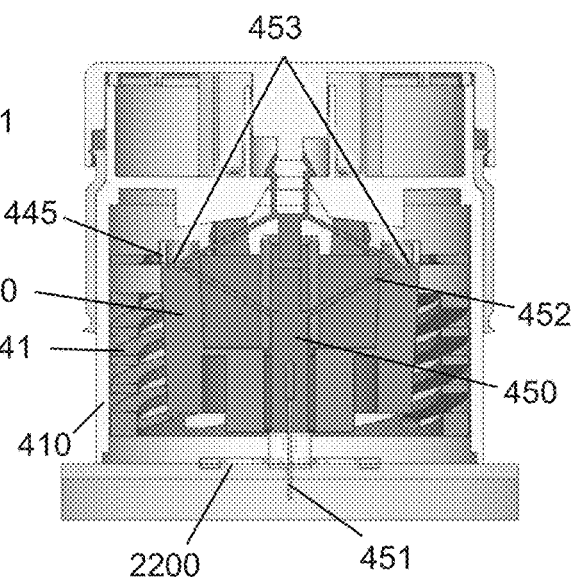
FIG. 29A  FIG. 29B
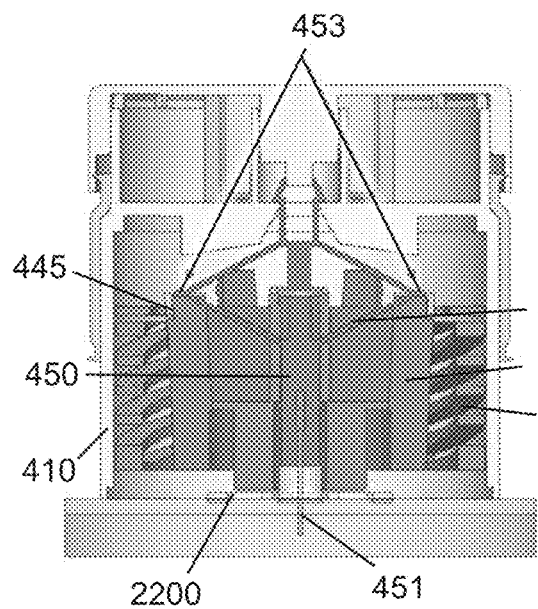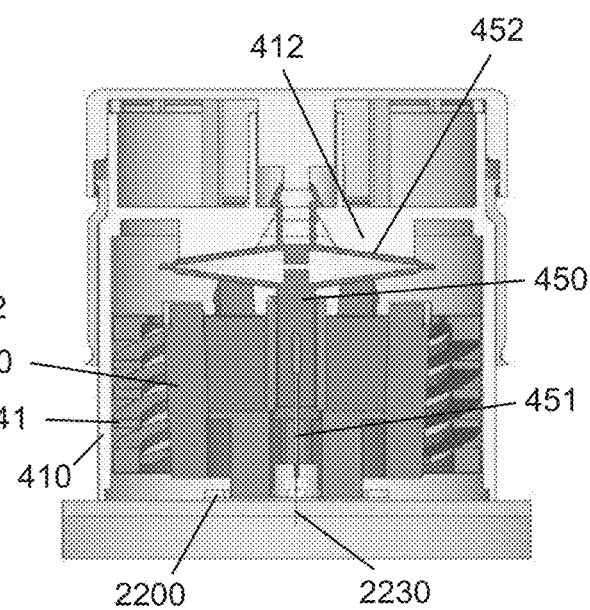
FIG. 29C  FIG. 29D

700 — 710

710

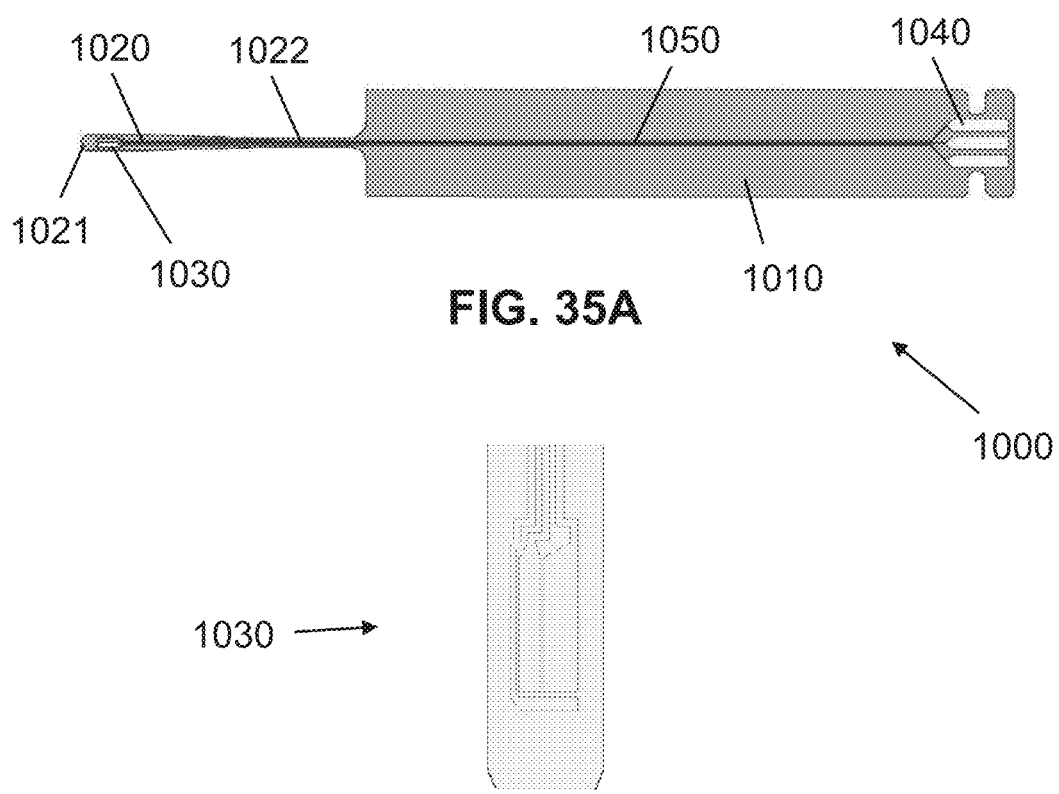
FIG. 35A
FIG. 35B
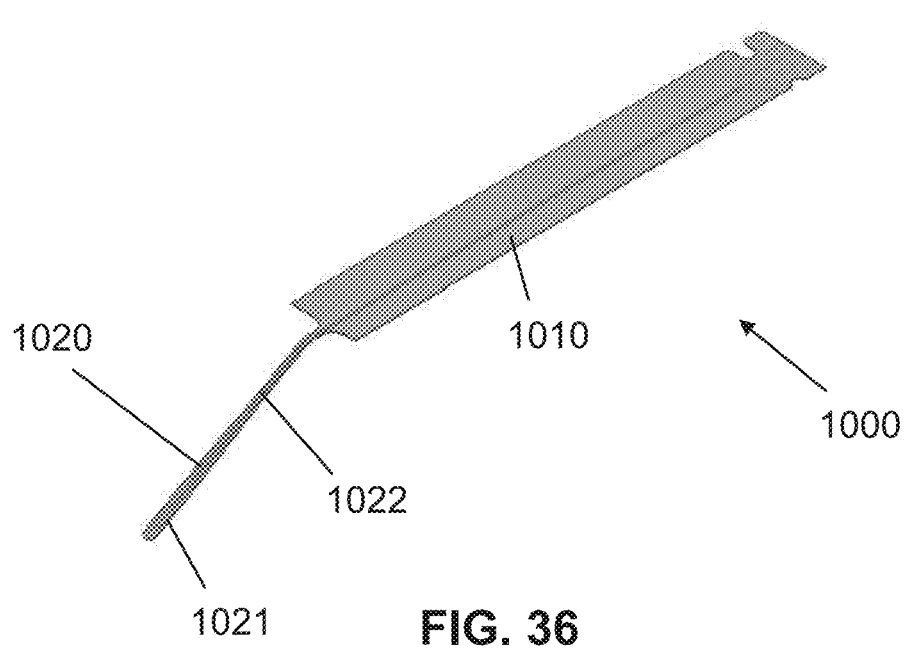
FIG. 36

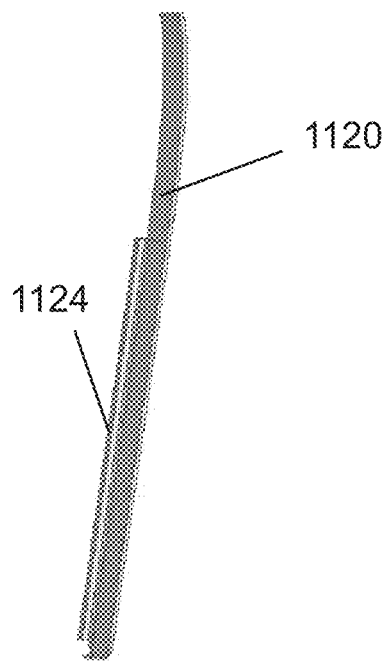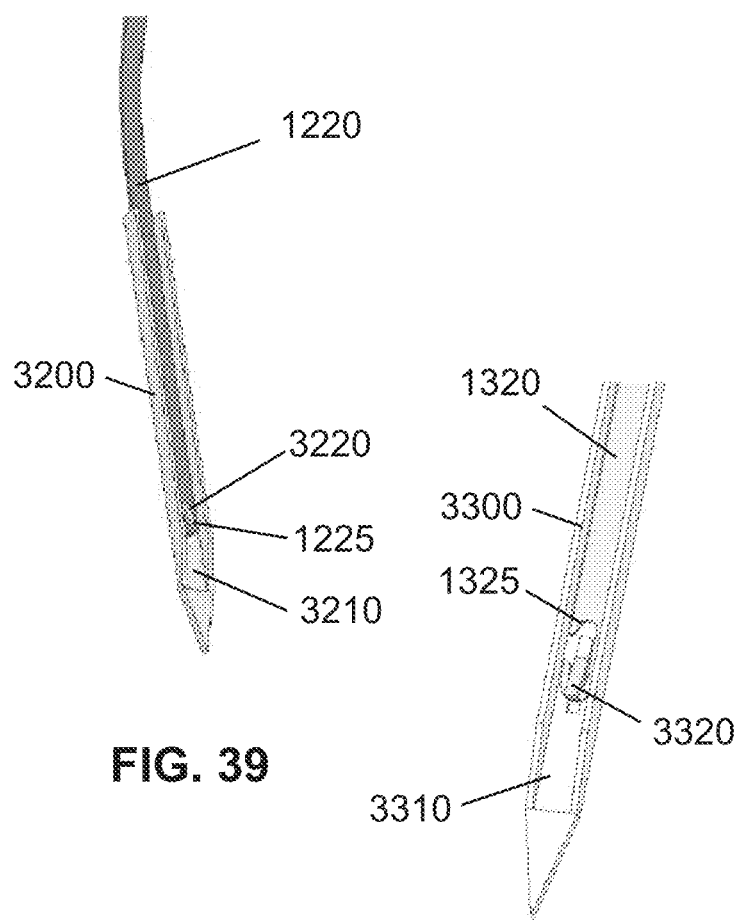
FIG. 38
FIG. 39
FIG. 40

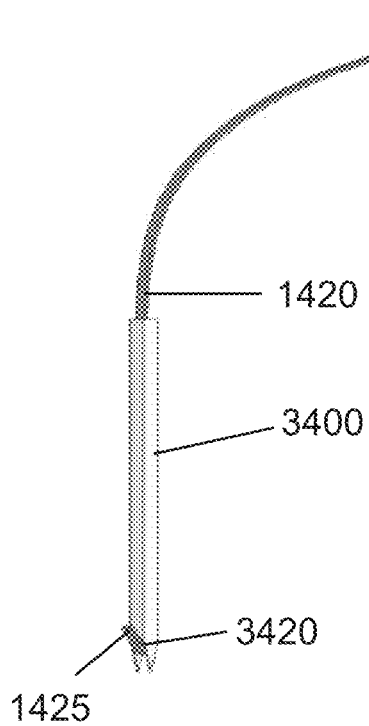 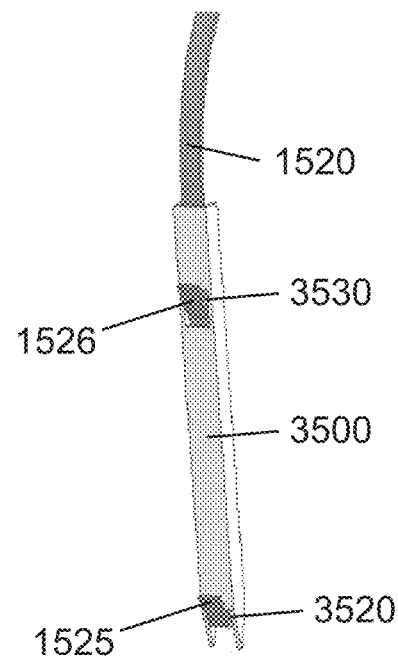
FIG. 41  FIG. 42
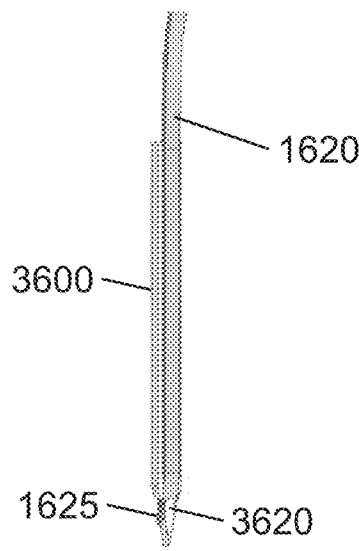 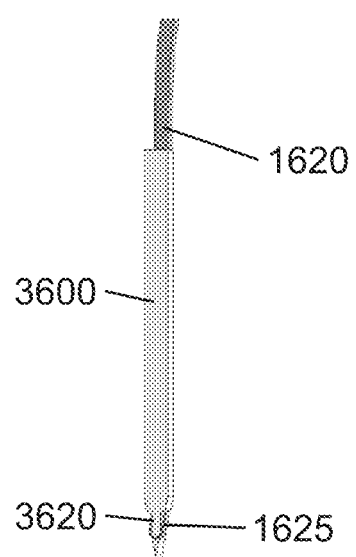
FIG. 43A  FIG. 43B

3710

3700

3720

APPLICATORS FOR GLUCOSE MONITORS, METHODS FOR APPLYING GLUCOSE MONITORS, AND GLUCOSE MONITORS FOR USE WITH SUCH APPLICATORS

CROSS-REFERENCE TO RELATED APPLICATION(S)

The present application claims priority to and the benefit of U.S. Provisional Patent Application No. 63/425,975, filed Nov. 16, 2022, the contents of which are hereby incorporated by reference in its entirety.

BACKGROUND

Field

The present disclosure relates to applicators and other devices for facilitating attachment or otherwise applying of monitors to a body of a subject, where the monitors may measure analytes, such as glucose, in the body of the subject. The present disclosure further relates to methods of using such applicators for applying monitors, and various glucose or other analyte monitors and/or design features thereof for use with such applicators.

Description of Related Art

Monitoring different analytes in the human body can used for various diagnostic reasons. In particular, monitoring glucose levels is important for individuals suffering from type 1 or type 2 diabetes. People with type 1 diabetes are unable to produce insulin or produce very little insulin, while people with type 2 diabetes are resistant to the effects of insulin. Insulin is a hormone produced by the pancreas that helps regulate the flow of blood glucose from the bloodstream into the cells int eh body where it can be used as a fuel. Without insulin, blood glucose can build up in the blood and lead to various symptoms and complications, including fatigue, frequent infections, cardiovascular disease, nerve damage, kidney damage, eye damage, and other issues. Individuals with type 1 or type 2 diabetes need to monitor their glucose levels in order to avoid these symptoms and complications.

Analyte monitors, and in particular, glucose monitors for the monitoring of glucose levels for the management of diabetes, are constantly being developed and improved. Although there are several platforms for monitoring analytes such as glucose available on the market, there is still a need to improve their precision, wearability, and accessibility to end-users. In addition, there is a desire to provide robust applicator tools that can help facilitate easier, less painful, less error-prone, and/or generally more effective application of glucose monitors to a patient's body, and in particular, continuous glucose monitors which may be attached to the patient's body for a more prolonged period of time, as well as glucose monitor features that can be used together with such improved applicators and applicator designs.

SUMMARY

Many continuous glucose monitors are intended to be worn on a patient's skin for a duration of multiple days or weeks. Most or all commercially available glucose sensors on the market today sense glucose in interstitial fluid (ISF) below the surface of the skin. Such sensing or monitoring therefore typically involves an initial step of inserting a sensor of the glucose monitor under the patient's skin. For the most part, this insertion step will involve puncturing the surface of the skin with a needle to provide access for inserting the sensor. Applicators will generally provide a means for inserting the sensor under the patient's skin via needle or other method. In addition, continuous glucose monitors may include a device body that remains adhered to the patient for a prolonged period of time as well. Applicators may also help facilitate proper attachment of the monitor body to the patient in a manner where the sensor is properly inserted and remains in place over the duration the monitor is intended to remain functional.

An aspect of one or more embodiments of the present disclosure is directed towards an applicator assembly for applying at least a portion of an analyte monitor. The applicator assembly includes a frame having a first end, a second end, a longitudinal axis extending between the first and second ends, and an opening at the second end, a resilient member positioned at least partially in the frame and having at least a first portion fixed relative to the frame and a second portion movable relative to the frame in a direction substantially parallel to the longitudinal axis, a needle movable together with the second portion of the resilient member, and a cap engageable with the frame to cover at least part of the opening. When the cap is connected to the frame at a first configuration, the second portion of the resilient member is at a first axial position relative to the frame, and the cap is restricted from separating from the frame. The cap is adjustable from the first configuration to a second configuration to increase a bias on the resilient member and to move the second portion of the resilient member to a second axial position relative to the frame that is farther from the opening. When the cap is at the second configuration, the cap is separable from the frame, while the second portion of the resilient member is configured to be held at the second axial position relative to the frame. The hold on the second portion of the resilient member is releasable, such that the bias on the resilient member advances the second portion of the resilient member and the needle towards the opening to a position where at least a tip of the needle extends axially out of the opening.

In some embodiments, the analyte monitor may be a continuous glucose monitor.

In some embodiments, the at least a portion of the analyte monitor may include a sensor member of the analyte monitor. A separate transmitter may be connectable to the sensor member after the sensor member is applied by the applicator assembly.

In some embodiments, the second end of the frame may define the opening and may extend substantially along a first plane, and the longitudinal axis of the frame may form an acute angle with the first plane. The acute angle formed between the longitudinal axis of the frame and the first plane may be approximately 40°. A concave channel that extends away from the first plane may be formed in the second end of the frame.

In some embodiments, the resilient member may further include a spring portion. The spring portion may be integrally formed with the first and second portions of the resilient member. When the cap is adjusted from the first configuration to the second configuration, the cap may be configured to directly increase the bias on the spring portion. The cap may include at least one ramp configured to directly engage the resilient member for biasing the spring portion.

In some embodiments, the cap may be rotatable relative to the frame to adjust the cap from the first configuration to the second configuration. The cap may be restricted from being separated axially from the frame when the cap is at the first configuration, and the cap may be separable axially from the frame when the cap is at the second configuration.

In some embodiments, when the needle is advanced to the position where at least the tip of the needle extends axially out of the opening, a stop may prevent further movement of the needle out of the opening. When the stop prevents further movement of the needle out of the opening, at least part of the second portion of the resilient member may be configured to move axially past the needle out of the opening to a position where the needle is covered by the second portion of the resilient member. When the needle reaches the stop, the needle may be configured to move back in a direction opposite the direction of advancement and away from the opening to a position where the needle may be covered by the second portion of the resilient member.

In some embodiments, the needle may be held by a needle holder that is movable independently from the resilient member. When the needle is advanced to the position where at least the tip of the needle extends axially out of the opening, the needle holder may have a resilient portion configured to move the needle in a direction opposite the direction of advancement and away from the opening.

In some embodiments, a kit may include an applicator assembly according to embodiments of the invention and at least a sensor member of the analyte monitor. The needle may have a slot that forms a longitudinal opening extending along a length of the needle. The sensor member may be positionable in the slot. The sensor member may include an end having a first width and a neck portion having a second width less than the first width. A width of the longitudinal opening on the needle may be less than the first width and greater than the second width. The sensor member may include a first engagement portion engageable with a second engagement portion of the needle, such that when the needle is advanced towards the opening of the frame, the first and second engagement portions may engage to pull the sensor member together with the needle towards the opening of the frame, while the first and second engagement portions may be configured to release when the needle is retracted away from the opening of the frame.

BRIEF DESCRIPTION OF THE DRAWINGS

Further features and advantages of the invention will become apparent from the description of embodiments by means of the accompanying drawings. In the drawings:

FIG. 13A shows a cross-sectional view of the applicator assembly according to the first embodiment with the striker or plunger in the biased state and with a button of the applicator assembly being depressed.

FIG. 13B shows a cross-sectional view of the applicator assembly according to the first embodiment in the state shown in FIG. 13A, with the cross-sectional view rotated relative to the cross-sectional view shown in FIG. 13A.

FIG. 13C shows a close-up of a portion of the applicator assembly shown in FIG. 13B.

FIG. 18 shows a perspective view of an applicator assembly according to a fourth embodiment, in a shipping or similar state prior to use by an end user.

FIG. 19A shows a cross-sectional view of the applicator assembly of FIG. 18 in the shipping state.

FIG. 19B shows a close-up of a portion of the applicator assembly shown in FIG. 19A.

FIGS. 29A to 29D show cross-sectional views of steps of operation of the applicator assembly after the button is depressed according to the fourth embodiment, including advancement and deployment of a needle on the needle carrier and retraction of the needle after deployment.

FIG. 35A shows a top view of a sensor of a monitor according to a first embodiment.

FIG. 35B shows a close-up view of sensing electrodes of the sensor of FIG. 35A.

FIG. 36 shows a perspective view of the sensor of FIG. 35A

FIG. 38 shows a perspective view of a sensor of a monitor according to a variation of the first embodiment shown in FIGS. 35A to 37B.

FIG. 39 shows a perspective view of a sensor of a monitor loaded on a needle according to a second embodiment.

FIG. 40 shows a perspective view of a sensor of a monitor loaded on a needle according to a third embodiment.

FIG. 41 shows a perspective view of a sensor of a monitor loaded on a needle according to a fourth embodiment.

FIG. 42 shows a perspective view of a sensor of a monitor loaded on a needle according to a fifth embodiment.

FIGS. 43A and 43B show perspective views of a sensor of a monitor loaded on a needle according to a sixth embodiment.

DETAILED DESCRIPTION

In the following detailed description, only certain embodiments of the subject matter of the present disclosure are described, by way of illustration. As those skilled in the art would recognize, the subject matter of the present disclosure may be embodied in many different forms and should not be construed as being limited to the embodiments set forth herein.

Figure 1A:
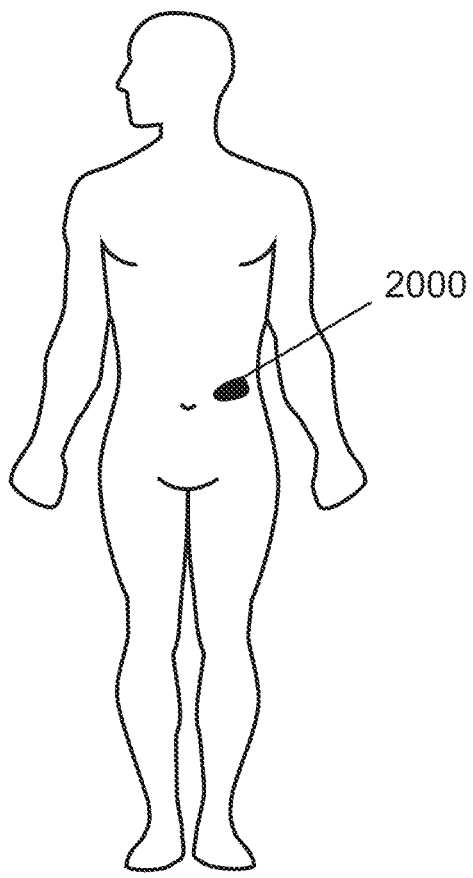
FIGS. 1A and 1B schematically show a human body with a monitor including an analyte sensor according to embodiments of the invention, where the monitor is attached at different positions on the body.
Figure 1B:
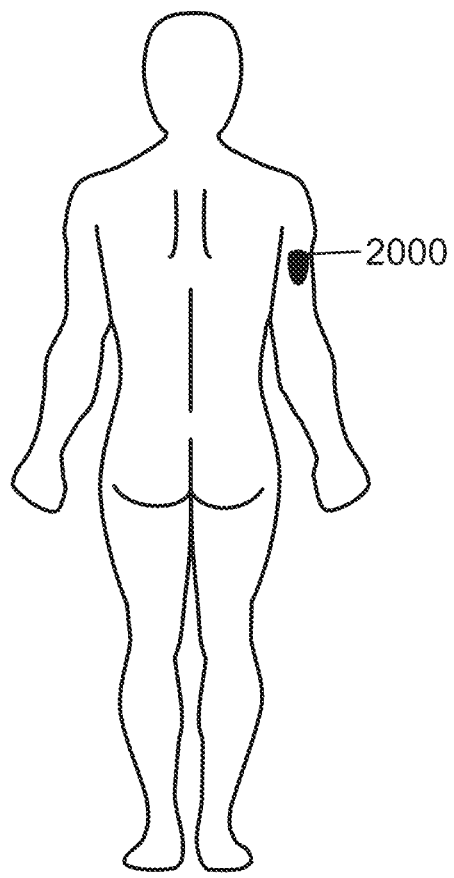

Monitors that include analyte sensors, such as glucose monitors, and particularly continuous glucose monitors, can be attached to a patient's body in different locations, in order to for example, improve glucose monitoring and/or a patient's comfort, since the continuous glucose monitors must remain adhered to the patient's skin, sometimes for a few days or more. FIG. 1A shows a first exemplary analyte monitor 2000 that is adhered to a patient's abdominal region, while FIG. 1B instead shows the exemplary analyte monitor 2000 adhered to a patient's arm. These are only meant to be example adhesion sites, and in other situations, this or a similar analyte monitor may instead be adhered or otherwise attached to other parts of the patient's body.

Figure 2:
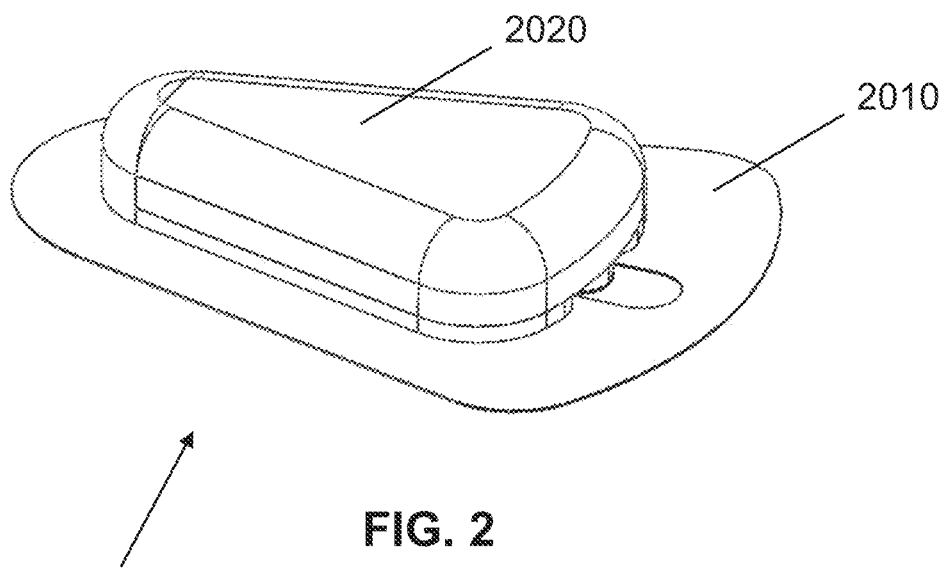
FIG. 2 shows a perspective view from above an exemplary monitor including an analyte sensor according to embodiments of the invention.
Figure 3:
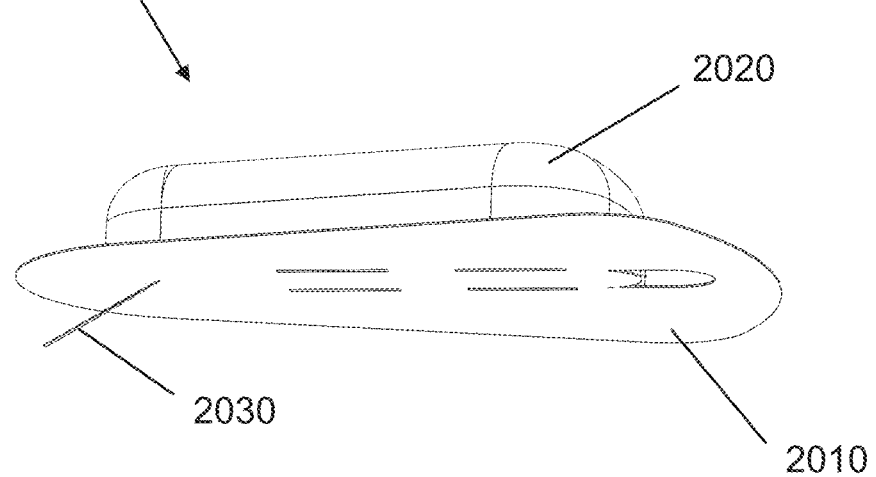
FIG. 3 shows a perspective from below the monitor of FIG. 2.

FIGS. 2 and 3 show different schematic views of an exemplary analyte monitor 2000, which can be a continuous glucose monitor, according to an embodiment of the invention. The continuous glucose monitor 2000 may include a base or cradle 2010 that may have an adhesive layer for adhering to a patient's skin, a transmitter 2020 for transmitting data to and/or from a location away from the monitor, and a sensor member 2030 which may include an integrated analyte sensing region such as a glucose sensor.

Figure 4A:
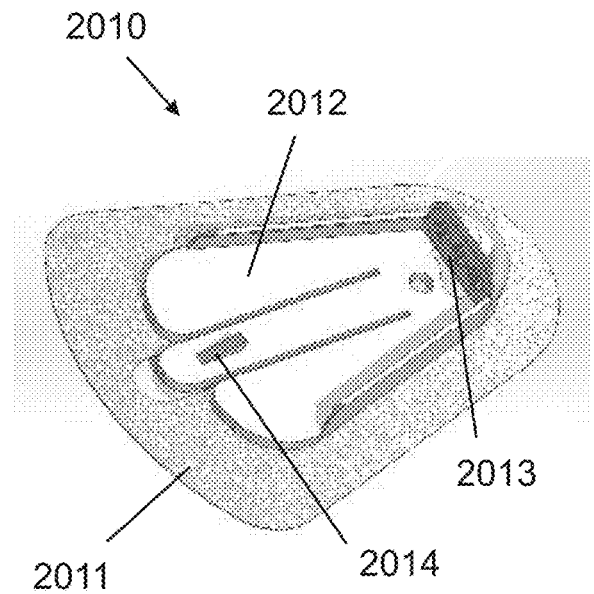
FIG. 4A shows a perspective view from above a cradle of an exemplary monitor, for example, the monitor of FIGS. 2 and 3.
Figure 4B:
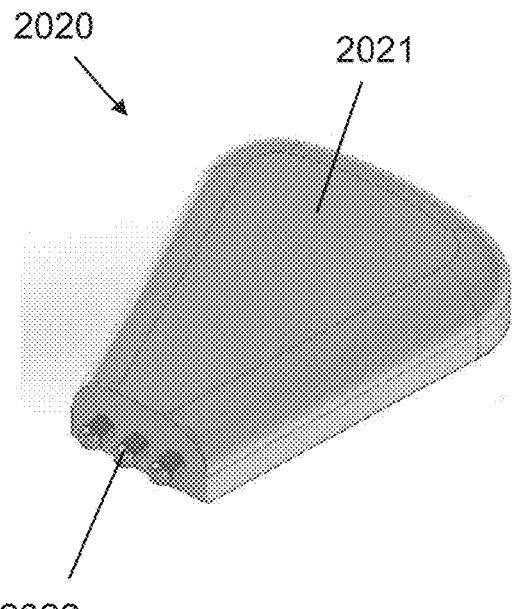
FIG. 4B shows a perspective view from above a transmitter of an exemplary monitor, for example, the monitor of FIGS. 2 and 3.

FIG. 4A shows the base or cradle 2010 of the monitor 2000. In the embodiment shown, the base or cradle 2010 is connectable and detachable from the transmitter 2020, but in other embodiments, the monitor may be a single integrated and connected unit. The cradle 2010 includes an adhesive or similar layer 2011 for connecting the cradle to the patient's skin. The adhesive layer may have a larger footprint or size compared to the rest of the cradle in order to facilitate a stronger connection to a patient or one that will last for a longer period of time, for example, multiple days or weeks. Other methods of attachment to a patient's skin may also be contemplated within the spirit and scope of the invention.

The cradle 2010 further includes a main body 2012 configured to facilitate attachment with the transmitter 2020. In the example shown, the body 2012 of the cradle is wedge-shaped to match a similar wedge shape of the transmitter 2020, but in other embodiments, the body and the transmitter may both be other shapes. In one region of the body, the cradle 2010 may further include contacts 2013 to facilitate an electrical connection with the transmitter 2020. In the embodiment shown, the contacts 2013 are located to one side of the cradle 2010, but in other embodiments, the contacts may be included in other regions of the cradle, based on the specific design and connection characteristics of the particular monitor. The cradle 2010 may also include a snap or other locking feature 2014 to facilitate a robust connection with the transmitter 2020 and reduce or eliminate occurrences of inadvertent detachment.

While not shown in FIG. 4A due to the angle of the perspective view, the cradle 2010 may further include the sensor member 2030 as an integrated component. For example, for at least some of the embodiments of applicator assemblies discussed below, the applicator assemblies are configured to attach cradles together with integrated sensors, so that actuation of the applicator assemblies will both deploy and properly position the sensor member under the patient's skin, as well as adhere the cradle to the outside of the patient's skin, in a single user step.

The base or cradle may further include other components, for example, at least some electronic circuitry to enable interconnectivity with the transmitter, and/or a battery.

The transmitter 2020 may include a main transmitter body 2021. The transmitter body 2021 includes at least a transmitter, and may further include other components such as a circuit board, memory, or other components for the transmitter to function properly. The transmitter 2020 further includes contacts 2022 configured to engage with the contacts 2013 on the cradle 2010, in order for example, to create a closed circuit for the monitor 2000 to activate and function properly.

Like the cradle, the transmitter may also include other components, for example, a battery. It will be recognized that the specific design of the monitor will dictate arrangement of different components and whether they are found on the cradle or the transmitter. For example, if a battery is housed in the cradle, a second battery will not be needed to be housed in the transmitter.

Figure 5:
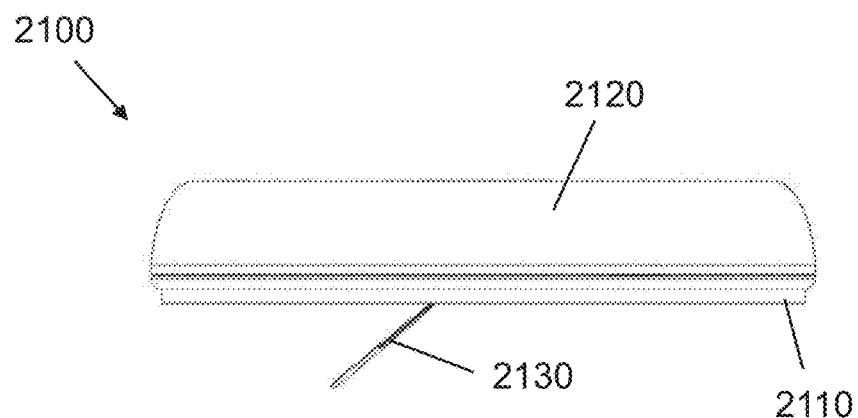
FIG. 5 shows a side view of another exemplary monitor including an analyte sensor according to embodiments of the invention.

As mentioned above, other embodiments of analyte monitors may be integrated single-piece monitors. By way of example, FIG. 5 shows a side view of another exemplary monitor 2100 including an analyte sensor according to embodiments of the invention. Monitor 2100 is a one-piece monitor which includes a base 2110 that may have an integrated adhesive layer, a body 2120 which may include some or all of the components discussed above with respect to monitor 2000, and a sensor member 2030. More or less components may be needed for proper functionality of such a one-piece monitor. For example, separate contacts may not be needed in one-piece monitor designs.

As mentioned above, in some embodiments, an applicator assembly is provided for attaching either a cradle or an entire monitor to a patient's skin, where the applicator assembly may serve to both properly insert and position a sensor member under a patient's skin, as well as to properly and securely adhere the cradle or monitor body to an outer surface of the patient's skin. Preferably, placement of the sensor member and the cradle or monitor body can both be accomplished together via a single action by the user, for example, an actuation of a button on the applicator assembly.

In general, an applicator assembly that includes a needle deployment to facilitate placement of a sensor member under the skin will further include an integrate sharps protection mechanism, that will retract the needle or otherwise shield the needle from the outside of the applicator assembly once the sensor has been deployed, to avoid injuries caused by the needle being exposed to the outside of the applicator assembly.

Figure 6:
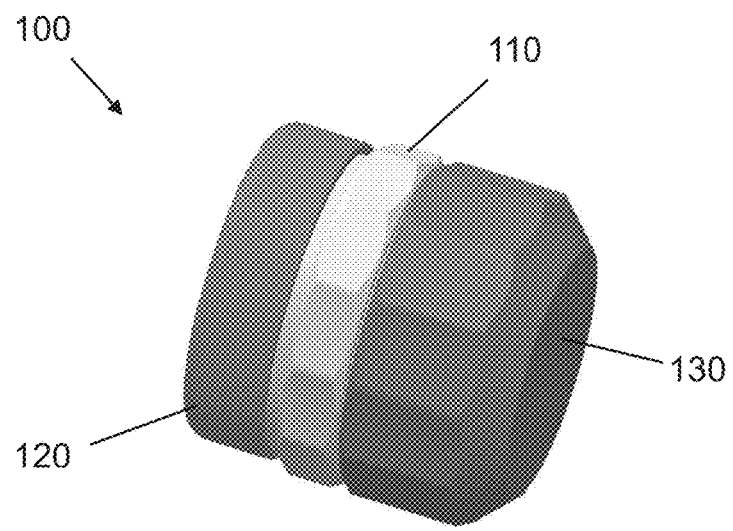
FIG. 6 shows a perspective view of an applicator assembly according to a first embodiment, in a shipping or similar state prior to use by an end user.
Figure 7A:
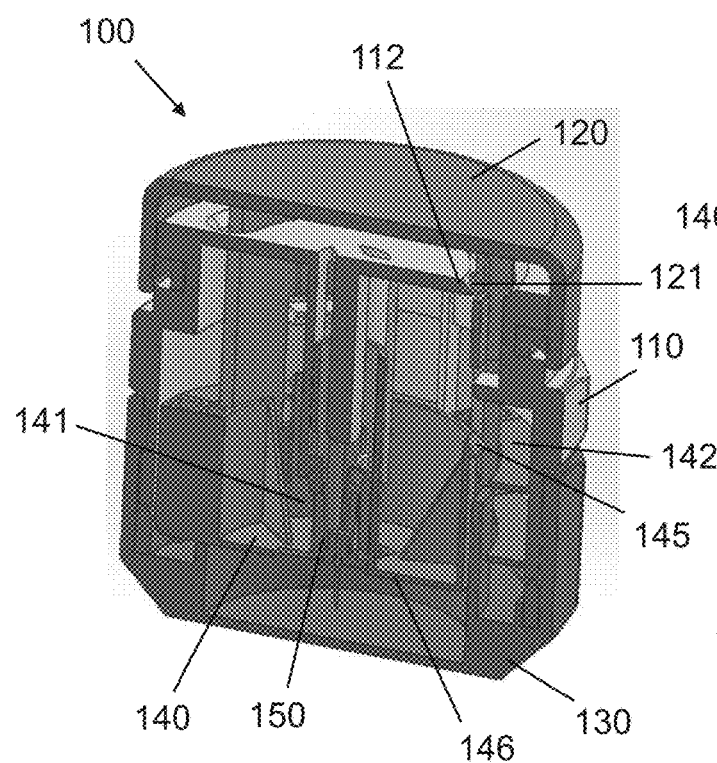
FIG. 7A shows a cross-sectional view of the applicator assembly of FIG. 6 in the shipping state.
Figure 7B:
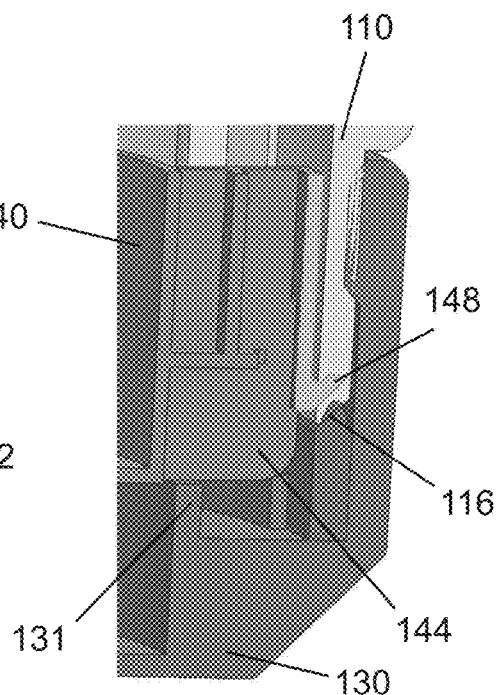
FIG. 7B shows a close-up of a portion of the applicator assembly shown in FIG. 7A.

A first embodiment of an applicator assembly is shown in FIGS. 6 to 15B. The applicator assembly 100 according to the first embodiment may be a molded spring applicator, where an internal spring mechanism and/or other parts of the applicator assembly may be injection molded or otherwise molded. The applicator assembly includes a main body or frame 110, a button 120, a cap 130, a plunger or striker 140, and a needle carrier 150. More or less parts may be included in other embodiments based on their specific designs. FIGS. 6 to 7B show the applicator assembly 100 in an initial shipping or storage state. Here, the applicator assembly is generally shipped as a sterile assembly, where an elastomer or other sterile barrier that may be found on the cap or on the frame helps facilitate keeping the assembly sterile. In some instances, plastic-on-plastic engagements, or engagements other than elastomer-based engagements, may be utilized to save on costs, but may be slower or more difficult to manufacture. Other types of barriers may also be utilized. The applicator assembly 100 may further be shipped in the initial shipping state in a sterile packaging.

In the embodiment shown, the applicator assembly 100 in its initial shipping state may be approximately 6 cm in length with the cap attached, and have an outer diameter of about 6 cm as well. In other embodiments, the size and shape of the applicator assembly may be larger or smaller, and/or have another shape, based at least in part on the size and shape of the wearable device (e.g., the cradle or the one-piece monitor) to be applied to the patient.

Figure 8A:
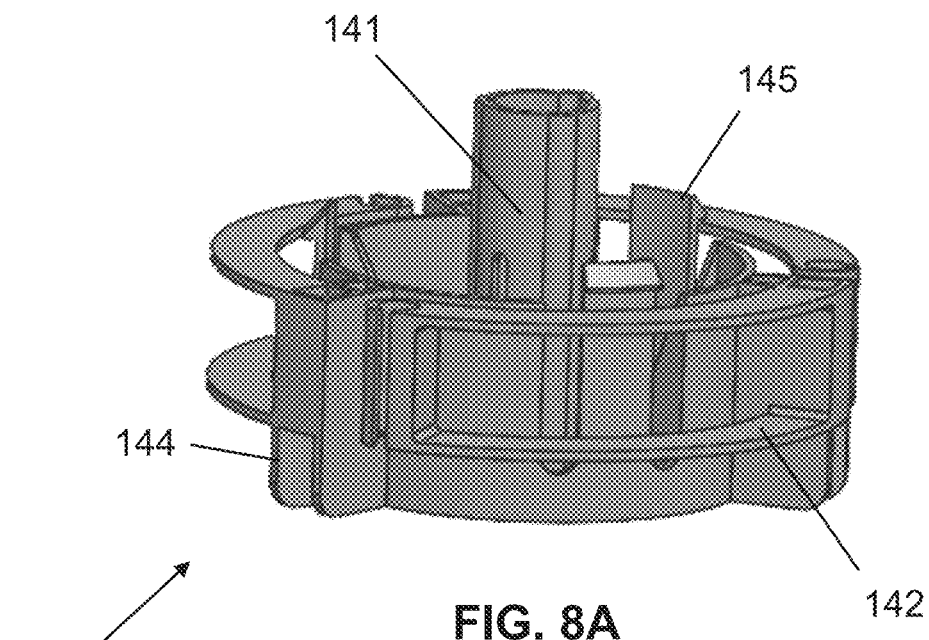
FIG. 8A shows a side view of a striker or plunger of the applicator assembly in an unbiased state according to the first embodiment.
Figure 8B:
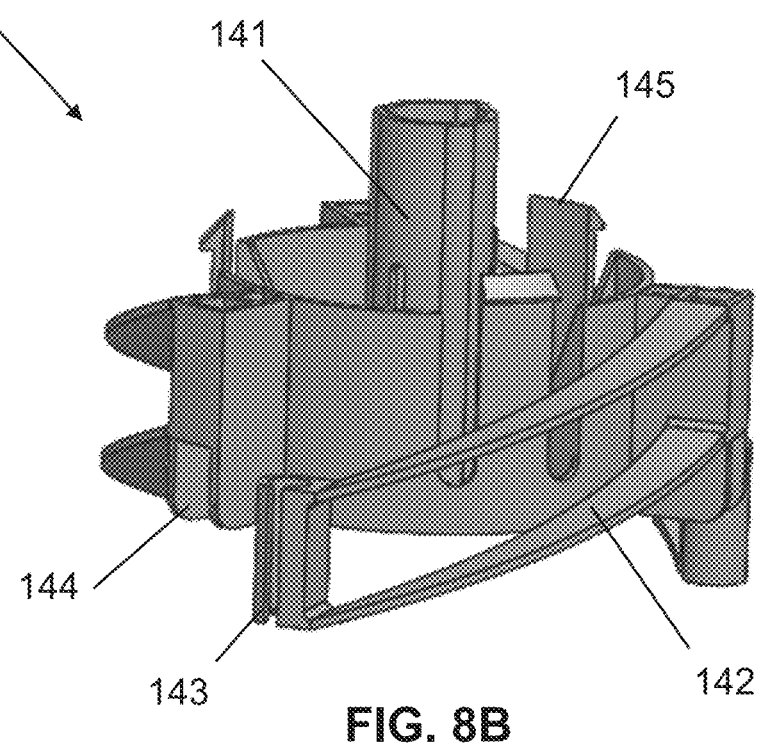
FIG. 8B shows the striker or plunger of FIG. 8 in a biased state.

FIGS. 8A and 8B show a striker or plunger 140 of the applicator assembly 100 according to the first embodiment. The plunger 140 forms a primary resilient member for the applicator assembly. The plunger 140 includes a central compartment 141 that may be sized and shaped to house the needle carrier 150 therein in an axially movable manner. For example, if the needle carrier has a substantially cylindrical shape or a similar shape with a circular cross-section, the central compartment 141 of the plunger 140 may similarly be shaped, for example, substantially cylindrical or conical. The plunger 140 may further include at least one resilient portion such as springs 142 to facilitate movement of the plunger 140 within the frame 110. The springs 142 in this embodiment are integrally formed with the rest of the plunger 140, and extend circumferentially around the plunger 140 to a free end 143 with an attachment means configured to attach to the frame 110. In the embodiment shown, the springs are molded, for example, injection molded, but may be formed in any other suitable manner. In addition, the springs 142 are integrally formed with the rest of the plunger 140, but in other embodiments may be separate parts that are connectable to the rest of the plunger 140. Here, the embodiment includes three springs, each extending slightly less than 120° around the circumference of the plunger 140, such that the three springs together extend around substantially an entire circumference of the plunger 140. In other embodiments, more or less springs may be included based on the desired strength and movement desired of the plunger 140 relative to the frame 110 to effectively deploy the needle and/or other components for delivering the wearable device. And in still other embodiments, other advancement mechanisms besides springs can also be used. At an end of the springs 142 opposite the free ends 143, the plunger 140 includes engagement portions 144 that are configured to move along ramps of the cap 130 in order to bias the springs, as will be described in greater detail below.

FIG. 8A shows the plunger 140 in an unbiased state, where the springs 142 are unbiased. FIG. 8B shows the plunger 140 in a biased or fully cocked state, where a preload is applied, for example, to the main body of the plunger 140, while the ends 143 of the springs 142 are held in place axially, resulting in the springs 142 biasing in an axial direction.

Figure 12:
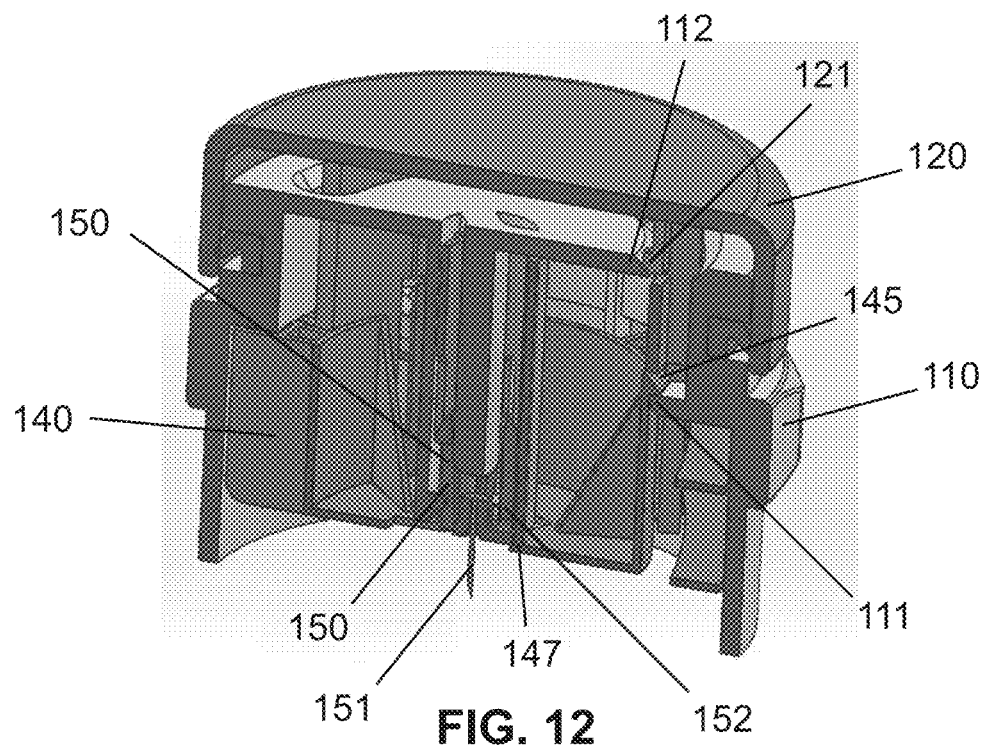
FIG. 12 shows a cross-sectional view of the applicator assembly according to the first embodiment with the striker or plunger in a biased state and with the cap removed.

At or near an upper end of the plunger 140, latches 145 may further be included, where the latches may be flexible, for example, may deflect radially inwardly. Furthermore, as labeled in FIG. 7A, a bottom surface 146 of the plunger 140 may be sized and shaped to effectively receive and hold a wearable device, for example, a cradle of a continuous glucose monitor, where downward advancement of the plunger 140 results in downward advancement of the wearable device as well, until the wearable device abuts against the patient's skin. For wearable devices where an adhesive is present, the adhesive will cause the wearable device to attach to and remain on the patient's skin, while the applicator assembly can be removed and detached from the wearable device. As best seen in FIG. 12, the bottom of the plunger 140 may also form an inner ledge 147, which limits downward or distal movement of the needle carrier 150 relative to the plunger 140, such that when the needle carrier 150 abuts against the ledge 147, the needle 151 may extend out of the bottom of the rest of the applicator assembly 100 a desired amount. In some embodiments, the plunger 140 may further include additional features, such as latches 148 (see, e.g., FIG. 7B) and posts 149 (see, e.g., FIG. 13C), which help facilitate operation of the applicator assembly 100, and which will be described in greater detail below.

Figure 9:
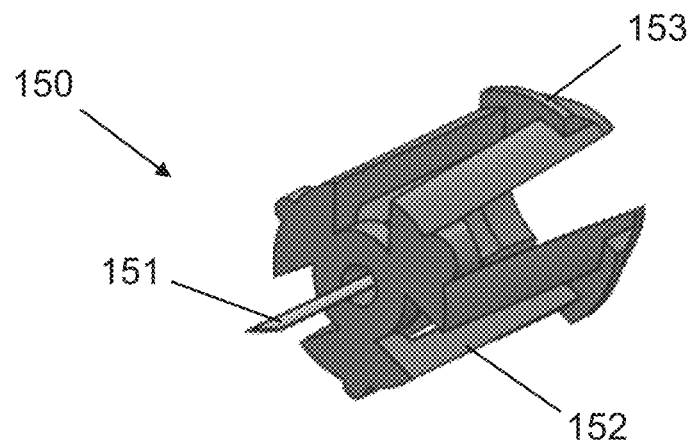
FIG. 9 shows a needle carrier of the applicator assembly according to the first embodiment.

A needle carrier 150 according to the first embodiment of the applicator assembly 100 is shown in FIG. 9. The needle carrier 150 includes a needle 151 that may be attached to a body 152. The carrier body in this embodiment may have a substantially circular outer profile, with stops or abutments 153 at one side thereof that are formed on ends of axially extending walls. The walls of the needle carrier may further be flexible, for example, radially inwardly and/or outwardly, such that the stops 153 are radially movable, for example, depending on the stroke position. The needle carrier should not be limited to the disclosed embodiment, and other needle carrier arrangements may also be used instead, based on the overall design of the applicator assembly.

Figure 10:
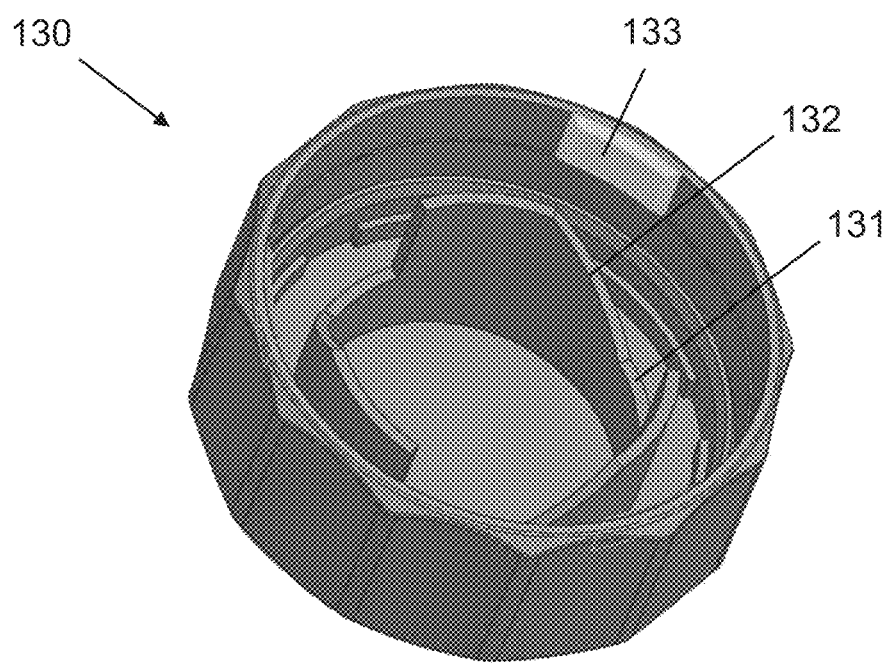
FIG. 10 shows a cap of the applicator assembly according to the first embodiment.

A cap 130 according to the first embodiment of the applicator assembly 100 is shown in FIG. 10. The cap 130 includes a circular track that extends around an inner chamber of the cap. The circular track may include shelves 131 and ramps 132, where the shelves 131 may extend parallel to a bottom surface of the cap 130, while the ramps 132 extend in an inclined manner from the shelves 131 towards the opening of the cap. In this embodiment, there are three shelves 131 and three ramps 132, to correspond to the three springs 142 of the plunger 140. However, in other embodiments, more or less shelves and/or ramps may be included based on the design of the applicator assembly, and in particular, based on the arrangement of the springs included in the applicator assembly. The cap 130 may further include a projection 133 or other form of engagement feature configured to engage a corresponding engagement feature on the frame (not shown). For example, in this embodiment, the projection 133 on cap 130 is rectangular in shape, and the cap 130 may include three similar projections 133 spaced equidistantly around the cap, for example, in 120° intervals. The frame may include an interrupted thread or track, for example, a track that extends slightly less than 120°, so that rotation of the cap 130 relative to the frame 110 over the length of the track will allow disengagement of the cap 130 from the frame 110. In other embodiments, the interrupted thread or track may be on the cap, and similar projections as those shown on the cap in this embodiment may be provided on the frame instead. In other embodiments, the track may be inclined or otherwise arranged to facilitate rotation of more than 120° even with three projections, for example, a 150° rotation to effect disengagement. Or any other arrangement where disengagement of the cap from the frame with less than a full 360° rotation of the cap is possible can be used. Allowing for detachment of the cap from the frame with less than a full 360° rotation may be beneficial to minimize or reduce relative movement between the parts and simplify detachment for the end user. In addition, detachment without excessive rotation may be needed due to the design of the ramps 132, which may make full 360° rotation of the cap difficult, as described in greater detail below.

During manufacturing, the cap 130 may be designed as a push-to-connect part, for example, where the cap 130 and/or the frame 110 may be slightly flexible, and/or via one-way ramps built into the structure of the parts, to facilitate easier connection of the parts together. However, axial disconnection of the parts may be undesirable, in order to properly operate the device and prevent user error, for example. Therefore, it should only be possible to disconnect the cap 130 from the frame 110 in this embodiment by rotation of the cap 130 and the frame 110 relative to one another. In another assembly method, the parts may simply be assembled the same way they are intended to be disassembled. For example, in this embodiment where removal of the cap requires approximately a 120° rotation of the cap 130 relative to the frame 110, assembly may simply require a simple bayonet action, where a quick engagement and rotation between the parts completes assembly. In yet other embodiments, other connection mechanisms can also be utilized.

Referring back to FIGS. 6 to 7B, in the initial shipping or storage state, the springs 142 may be completely unbiased, or may be biased only a small amount. A slight preload from the time of manufacture may be desirable, so long as there is not enough load to cause creep of the parts. In addition, referring specifically to FIG. 7B, a slight preload on the springs 142 may ensure that plunger 140 is positioned slightly axially higher relative to frame 110, which may prevent latches 148 from unintentionally engaging ledge 116 on the frame 110. Latches 148 are intended to engage ledge 116 after firing of the applicator assembly, in order to act as a lock to prevent retraction of the plunger 140 back into the frame 110, so that the plunger 140 can be used as a sharps guard as described in greater detail below. In some embodiments, an undercut may be included to house the latches 148 in the shipping state, to prevent a preload acting on the latches 148. In other embodiments, the springs may be biased or preloaded a greater amount, for example, fully biased in a "ready to fire" state, at manufacture.

As previously mentioned, a sterile barrier may be formed between the cap and the frame to seal the interior of the applicator assembly and keep it sterile. In addition, a similar seal may be formed between the button and the frame for the same purpose. Furthermore, the cap or another portion of the assembly may include a safety mechanism to prevent the button from inadvertently misfiring before the wearable device is ready to be deployed.

Figure 11:
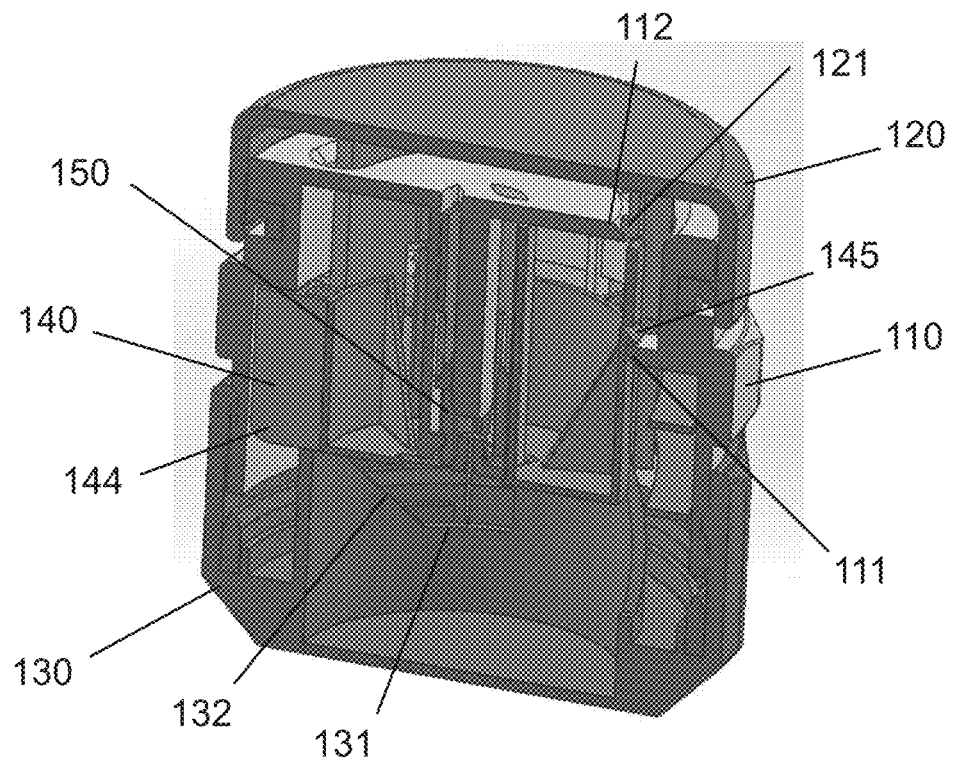
FIG. 11 shows a cross-sectional view of the applicator assembly according to the first embodiment after a step of cocking or otherwise biasing the striker or plunger.

FIGS. 11 and 12 illustrate the applicator assembly 100 in a ready-to-fire state. Prior to cocking of the applicator assembly, as best seen in FIGS. 7A and 7B, the engagement portions 144 of the plunger 140 rest on the shelves 131 of the cap 130. Referring then to FIGS. 10 and 11, an unscrewing or otherwise rotation of the cap 130 relative to the frame 110 will cause the engagement portions 144 of the plunger to move up the ramps 132, e.g., in a proximal direction towards the button 120, while the ends 143 of the springs 142 are held in the same axial position relative to the frame 110 by engagements 113 (see, e.g., FIG. 13B). This results in a biasing of the springs 142 in the manner shown in FIG. 8B, such that the base of the plunger 140 is held at the higher position shown in FIG. 11. The plunger 140 is moved upwards until latches 145 snap over or otherwise engage ledge 111 of frame 110 to hold the body of the plunger 140 at this higher cocked position. At the same time, the needle carrier 150 is also moved upwards together with the body of the plunger 140 via the engagement at the ledge 147. At the fully cocked position shown in FIGS. 11 and 12, the free end of the needle will be axially recessed from a lower or distal end of the frame 110, such that the needle will not extend axially out of the applicator assembly 100 until the button 120 is depressed. Rotation of the cap until the plunger 140 is at the fully cocked position may coincide with the projections 133 of the cap 130 aligning with the openings on the tracks of the frame 110, to allow for removal of the cap 130 from the rest of the applicator assembly 100 only when the plunger 140 has been fully cocked and latches 145 have snapped into place. After removal of the cap 130, as shown in FIG. 12, the applicator assembly is ready for use to apply an attached wearable device (not shown).

Loading the applicator assembly 100 via rotational cocking provides a number of benefits over pre-loaded springs. For example, storing a plastic spring in a cocked state for prolonged periods of time may degrade the spring, as cold flow and creep can negatively affect performance of the spring. Having the user cock the spring while removing a sterile barrier cap eliminates the cold flow risk by only cocking the plastic firing spring at the time of use. Furthermore, integrating the spring cocking into the barrier removal process makes the cocking invisible to a user, and may also provide a mechanical advantage to achieve higher cocking forces for higher velocity needle insertion.

Steps of firing the applicator assembly 100 are shown in FIGS. 13A to 15B. Actuation or firing of applicator assembly 100 is designed as a one-step process for the end user, for example, by depression of button 120 relative to frame 110. In practice, after removal of cap 130, the user places the applicator assembly 100 at the desired location of attachment of the cradle or other wearable device, with the open end facing towards the skin. Once a desired deployment location is selected, the button 120 is depressed towards the skin, which results in both the firing of the applicator assembly 100 to place the wearable device on the skin and the sensor under the surface of the skin, and the deployment of the sharps guard thereafter to retract and/or otherwise conceal the needle 151 for safety purposes.

Referring first to FIGS. 13A to 13C, when button 120 is depressed, posts 122 of button 120 are moved downward relative to frame 110 until they engage latches 145 of plunger 140. A bottom surface of posts 122 may serve to push latches 145 radially inwardly to make latches 145 disengage from ledges 111 of frame 100. One or both of the top of latches 145 and/or the bottom of posts 122 may be tapered or inclined to facilitate the radially inward movement of the latches 145. The button 120 itself may only move down a small fixed axial distance, and another latch, for example, latch 121 on button 120, may engage ledge 112 of frame 110 to hold the button 120 at its lower depressed position, in order to ensure deployment of the plunger 140. In some embodiments, engagement of the latch or latches 121 with the ledge 112 may result in an audio or tactile click to provide feedback to the user that the button has been successfully fully depressed. In some embodiments, the latches 121 may differ in number and size, for example, may be longer or shorter than shown in the figures, depending on the specific design of the applicator assembly.

When the latches 145 of plunger 140 are urged inwardly and disengage from ledge 111 of frame 100, the body of the plunger 140 is no longer held in the upward position, and the bias of springs 142 serve to urge the body of plunger 140 downwards. The downward movement of the plunger 140 will also result in the downward movement of the wearable device or other payload that is connected to the bottom 146 of the plunger 140 towards the user's skin. As best seen in FIGS. 13B and 13C, the needle carrier 150 including the needle 151 are also urged downward together with the plunger 140. The walls of the needle carrier 150, including the latches 153, are blocked from deflecting radially inwardly by a post 114 on the frame 100, and additional posts 149 on the plunger push down on the tops of latches 153, so that plunger 140 and needle carrier 150 translate downwardly together towards the user's skin. Due to the presence of post 114, even if the tops of latches 153 are inclined, the downward pressure applied by posts 149 of plunger 140 will result in downward movement of the needle carrier 150 because the post 114 prevents inward movement of the latches 153 to escape the downward force of posts 149.

Figure 14:
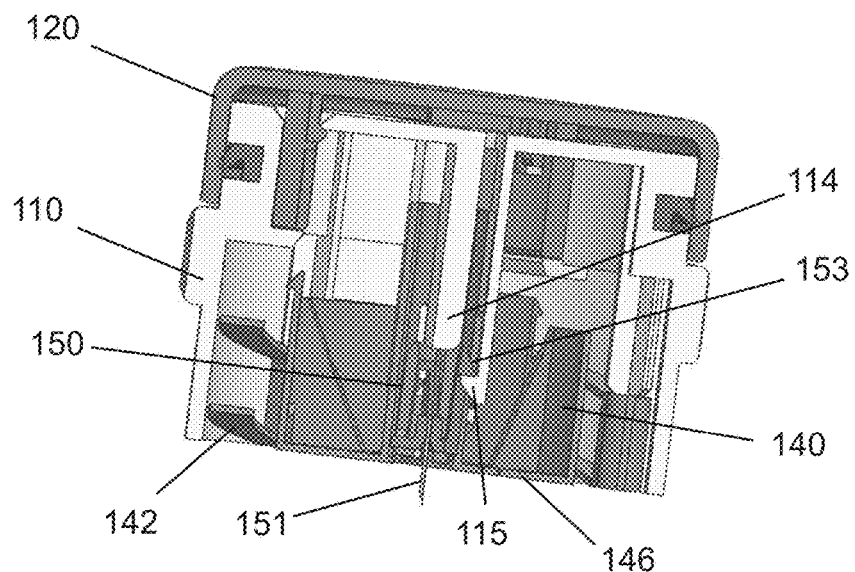
FIG. 14 shows a cross-sectional view of the applicator assembly according to the first embodiment after the button is depressed and the striker or plunger is released such that a needle of a needle carrier of the applicator assembly is advanced and deployed for insertion into a patient's body.

In FIG. 14, the needle carrier 150 has reached its lowermost position during the deployment process. In this position, the bottom 146 of the plunger 140 will urge the wearable device or other payload against the user's skin, while the needle 151 and any loaded sensor member is pushed through the skin to a desired position under the surface of the skin. The length of the needle 151 will change depending on the size and configuration of the applicator assembly, the desired depth and positioning of the sensor member, and on the size and shape of the wearable device or other payload, for example, the shape of the cradle to be delivered together with the sensor member, and how the payload is loaded and held by the applicator assembly. In the embodiment shown, the needle is inserted perpendicularly to the user's skin surface into the skin. In other embodiments, such as some discussed below, the needle may be inserted into the user's skin at an angle relative to the surface of the skin. Here, further downward movement of the needle carrier is prevented due to engagement of the latches 153 on the needle carrier 150 with the ledge 115 of the frame 110. At this height, the walls of the needle carrier 150 may also be axially clear of the post 114, which will allow the walls to deflect inward slightly in order to allow the posts 149 of the plunger 140 to pass by them, thereby allowing the plunger 140 to continue to move downwards relative to the frame 110 while the axial position of the needle carrier 150 relative to the frame 110 remains the same.

Figures 15A, 15B:
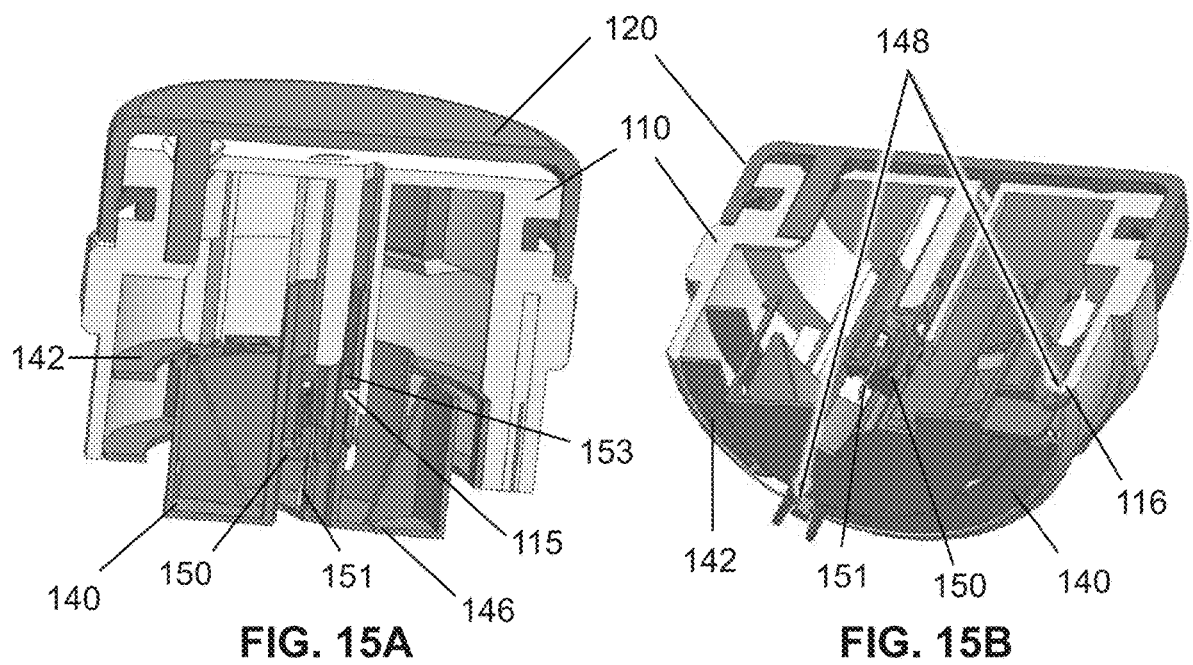
FIG. 15A shows a cross-sectional view of the applicator assembly according to the first embodiment after deployment of the needle, where the striker or plunger is further advanced to conceal the needle from the outside of the applicator assembly.
FIG. 15B shows a cross-sectional view of the applicator assembly according to the first embodiment in the state shown in FIG. 15A, with the cross-sectional view rotated relative to the cross-sectional view shown in FIG. 15A.

After the downward movement of the needle carrier 150 relative to the frame 110 is stopped, the bias on the springs 142 will continue to force the plunger 140 downwards relative to the frame 110 and the needle 151 without any additional user input. Since the bottom 146 of the plunger 140 is already pressed against the user's skin, or against the payload which is held against the user's skin, additional movement of the plunger 140 relative to the frame 110 results in pushing of the frame 110 and the needle 151 away from the user's skin, effectively pulling the needle out of the user's body. Furthermore, since the needle 151 is retracted axially relative to the plunger 140, the body of the plunger 140 acts as a sharps guard to shroud or surround the needle 151 once the plunger 140 is fully advanced relative to the frame 110 and the needle 151, as shown in FIGS. 15A and 15B. In this position, the needle 151 is safely housed within the plunger 140 after deployment. Here, the springs 142 may be able to return to or close to their unbiased states, where latches 148 snap under or otherwise engage ledges 116 at or near a bottom end of the frame 116, to prevent the plunger 140 from moving back into the frame 110. Since the positions of both the plunger 140 and the needle 151 are fixed relative to the frame 110 in this final position, the needle 151 is prevented from being exposed to the outside of the applicator assembly. Here, the cap 130 can be replaced over the bottom of the applicator assembly for additional protection and disposal.

Figure 16A:
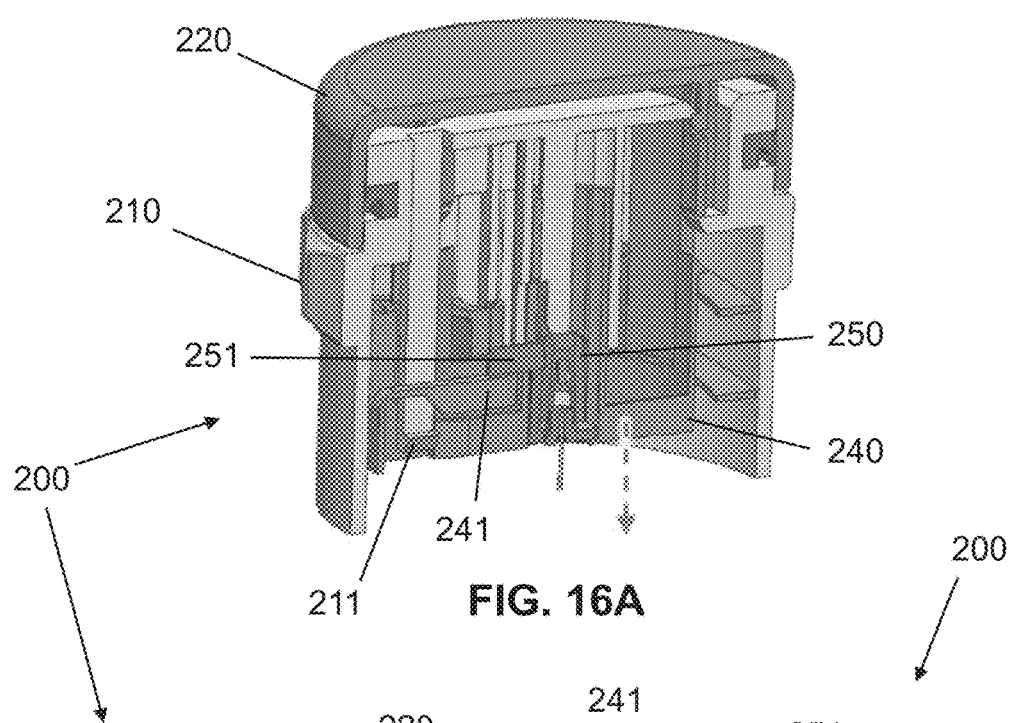
FIGS. 16A to 16C show cross-sectional views of steps of operating an applicator assembly according to a second embodiment.
Figure 16B:
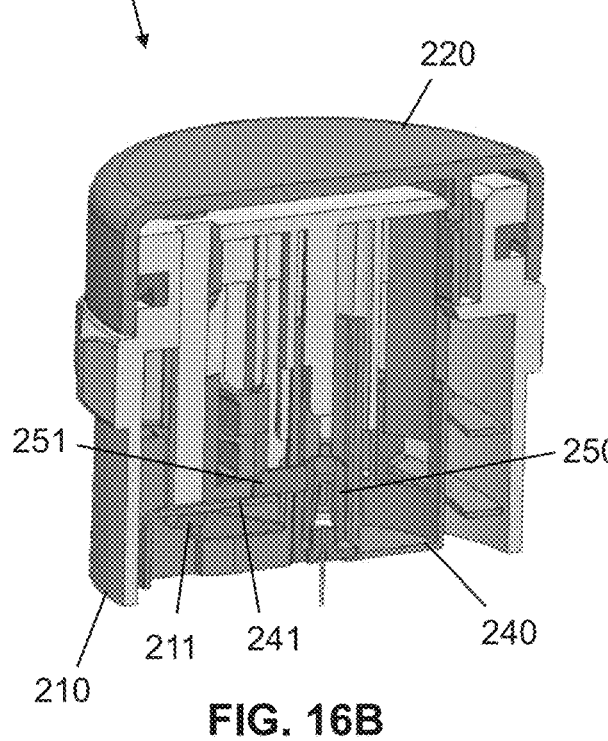
Figure 16C:
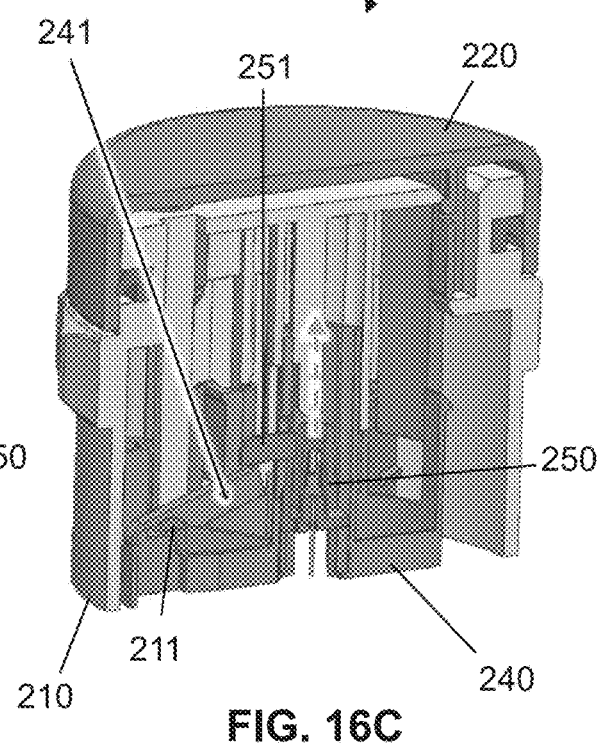

A second embodiment of an applicator assembly is shown in FIGS. 16A to 16C. Parts, portions, and operations of the second embodiment of the applicator assembly that are similar to the first embodiment will not be repeated.

The applicator assembly 200 according to the second embodiment has, similar to the first embodiment, a frame 210, a button 220, a striker or plunger 240, and a needle carrier 250. The applicator assembly may further include a cap (not shown), which may function similarly to the cap of the first embodiment. In the second embodiment, the shipping, loading, and cocking of the applicator assembly 200 may be substantially similar to that of the first embodiment. The applicator assembly 200 differs from the first embodiment via a lever retraction mechanism between the plunger 240, the frame 210, and the needle carrier 250.

FIG. 16A shows the downward advancement of the body of the plunger 240 and the needle of the needle carrier 250 towards the user's skin. Downward movement of the plunger 240 will result in axial movement of a lever ejector 241 or other similar mechanism towards a ledge, undercut, or similar projection 211 on the frame 210. When the needle of the needle carrier 250 pierces the user's skin and reaches its final depth, as shown in FIG. 16B, the lever ejector 241 of the plunger 240 hits the projection 211 and deflects upwards at the end of the stroke or advancement of the plunger 240, as shown in FIG. 16C. The deflection may be facilitated by a traditional hinged connection, a living hinge, or other similar hinge connecting the lever ejector 241 with the rest of the plunger 240. The last portion of the downward movement of the plunger 240 will result in pivoting of the lever ejector 241 upwards. An upper side of a free end of the lever ejector 241 engages a radial projection 251 on the needle carrier 250, which in turn forces the needle carrier 250 and the connected needle upwards relative to both the plunger 240 and the frame 210. Under this arrangement, the lever mechanism retracts the needle carrier 250 and needle at the end of the stroke, in lieu of or in addition to further advancement of the plunger 240.

In the embodiment disclosed, the plunger 240 includes three lever ejectors 241 that act on three projections 251 on the needle carrier 250, but in other embodiments more or less lever ejectors and projections may be provided instead. In addition, in the arrangement shown, leverage amplification results in the lever mechanism providing a 3:1 movement ratio, where the last 1.67 mm of downward movement of plunger 240 relative to frame 210 translates to or otherwise results in 5 mm of upward movement (i.e., retraction) of the needle carrier 250 and connected needle relative to the frame 210, resulting in 6.67 mm total axial retraction of the needle carrier 250 and connected needle relative to the plunger 240. This results in a sufficient retraction of the needle into the plunger 240, with less movement needed by the plunger relative to the frame 210, and less protrusion of the plunger 240 from the bottom end of the frame 210 in the final state.

Other modifications are also conceivable, for example, varying the leverage amplification to provide a larger stroke or increased retraction of the needle carrier, with limitations to such modifications being size tradeoffs for example, of the entire applicator assembly. In addition, additional modifications may also be needed, in order to achieve a sufficient force needed for the lever to reliably retract the needle carrier. Various different dimensions and other factors may also contribute to providing a reliable working model of this lever retraction variation of the applicator assembly.

A third embodiment of a needle carrier is schematically shown in FIGS. 17A to 17D. The third embodiment of the needle carrier 350 functions similarly to the needle carrier 250 in the second embodiment in that both include mechanisms to facilitate retraction of the needle carrier relative to the rest of the applicator assembly, for providing an effective sharps guard configuration after deployment. However, the schematic illustrations in FIGS. 17A to 17D show an embodiment where living hinges formed on the needle carrier itself interact with other features of the applicator assembly device of the third embodiment to eject the needle after deployment.

In the third embodiment in FIGS. 17A to 17D, a needle carrier 350 includes a needle 351 and at least two radial projections 352. The radial projections 352 may be connected to the main body of the needle carrier 350 via a living hinge or similar hinge. The living hinge may only allow bending or flexing of the projections 352 in one axial direction, for example, axially downwards, relative to the main body of the needle carrier 350, and may prohibit or otherwise restrict pivoting of the projections 352, for example, in an opposite upward direction. In addition, the living hinge may only release or otherwise bend upon application of a sufficient force or counterforce on the projections 352.

Figure 17A:
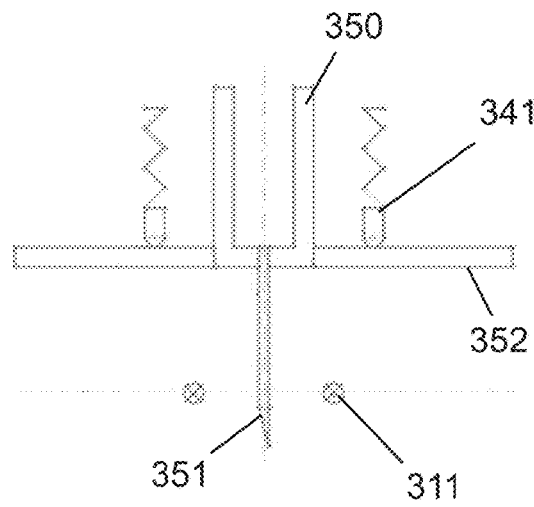
FIGS. 17A to 17D show schematic views of a needle carrier and retraction mechanism associated therewith according to a third embodiment.
Figure 17B:
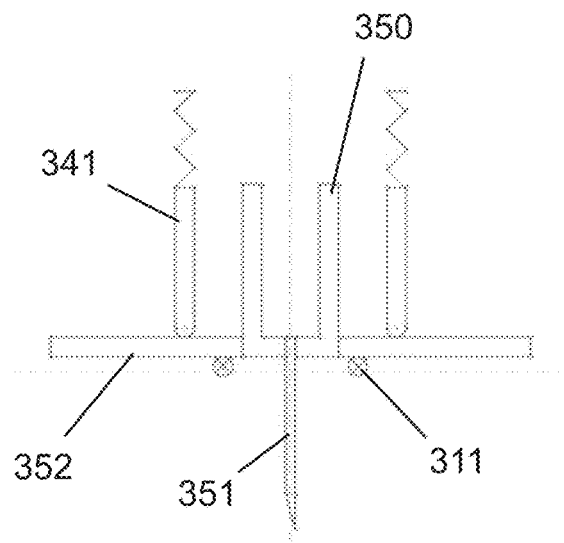
Figure 17C:
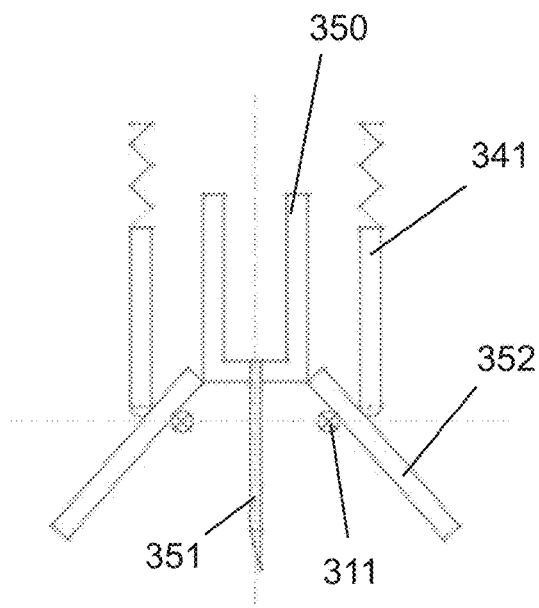
Figure 17D:
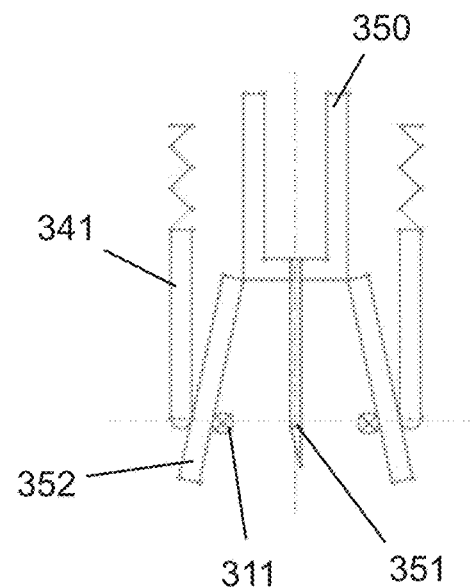

Similar to previous embodiments, as shown schematically in FIG. 17A, a portion 341 of a spring-based or otherwise advanced plunger may engage the needle carrier 350 to push the needle carrier 350 and the connected needle 351 downwards. The plunger 341 may act on the projections 352 of the needle carrier 350 in some embodiments, and provide a small enough force that the living hinges are not activated and the projections do not bend relative to other portions of the needle carrier 350. After the needle punctures the user's skin and has been inserted to a desired depth, as shown in FIG. 17B, a bottom surface of the projections 352 may engage a portion 311 of the frame of the applicator assembly, for example, a fixed abutment or undercut, at or near the end of the stroke or deployment, where the plunger 341 continues to travel downwards and the further downward force provided by the plunger 341 on the projections 352 will force the living hinges to actuate and the projections to bend downwards, with the portion 311 of the frame serving as an axis or pivot point for the projections 352, for example, as shown in FIG. 17C. Here, the leverage caused by the projections 352 against the pivot point 311 of the frame causes the main body of the needle carrier 350, and the connected needle 351, to retract back upwards relative to the other portions of the applicator assembly. Further downward force applied by the plunger 341 on the outside of the projections 352 will cause additional upward movement of the main body of the needle carrier 351, and the connected needle 351, upwards as shown in FIG. 17D. The relative dimensions of the projections 352, the living hinge, and the positioning of the plunger 341 and the pivot point 311 of the frame can be selected to facilitate a sufficient retraction of the needle carrier 350 to a safe and fully shielded final position.

It should be noted that under this design, efficiency may be lower compared to other models, where employing molded springs in some places may be an option to improve efficiency. In addition, while the projections 352 and hinges are provided near a bottom of the needle carrier 350 in the schematics shown, the hinges and projections may be higher up on the needle carrier in other embodiments to avoid the projections 352 swinging into and hitting the user's skin when the hinges are actuated and bent. There may be other drawbacks and/or technical risks to employing living hinges, for example, the assembly may jam if friction is excessive. Or controlling the stiffness of the hinge levers may be challenging to regulate consistently as well, since bending of the living hinges relies on relative forces, unintentional bending may occur before intended, or bending may not be effected at all in some instances. Therefore, it may be difficult to design an assembly incorporating living hinges that performs consistently and robustly.

An applicator assembly 400 according to a fourth embodiment is shown in FIGS. 18 to 30B. Parts, portions, and operations of the fourth embodiment of the applicator assembly that are similar to the previous embodiments will not be repeated. In particular, the external profile and size of the applicator assembly 400 according to the fourth embodiment is arranged similarly to the profile and size of applicator assembly 100 according to the first embodiment.

The applicator assembly 400 includes a main body or frame 410, a button 420, a cap 430, a striker or plunger 440, a needle carrier 450, and an overmolding 460. Like the first embodiment, the applicator assembly 400 as shown in an initial shipping state in FIGS. 18 to 19B is a sterile assembly.

Figure 20A:
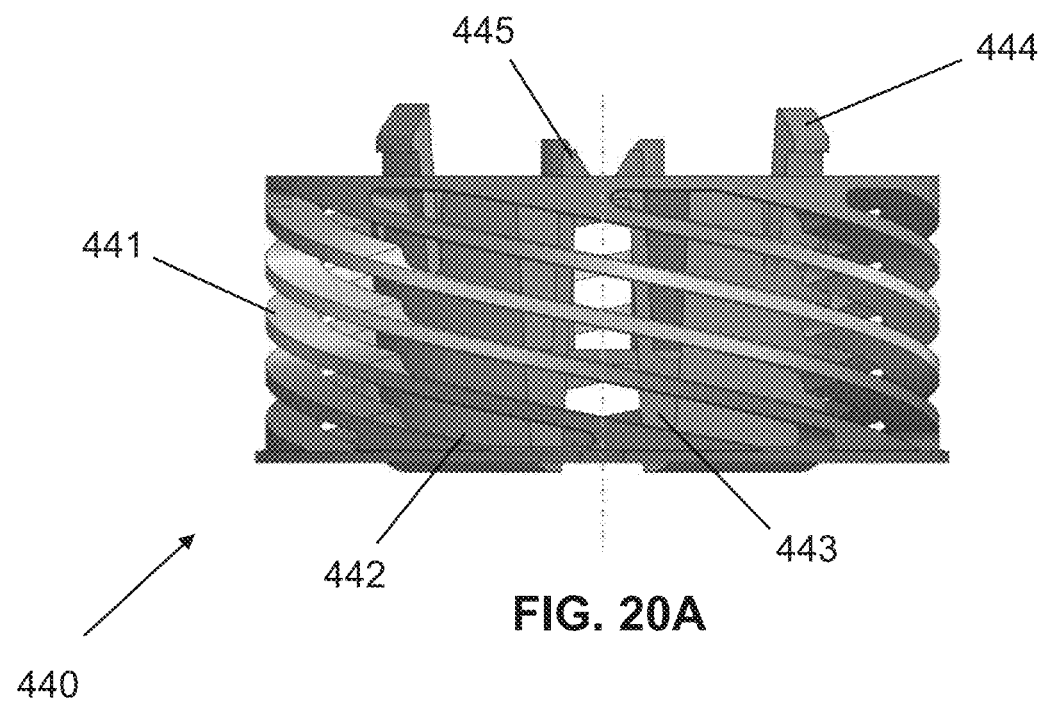
FIG. 20A shows a side view of a striker or plunger of the applicator assembly in an unbiased state according to the fourth embodiment.
Figure 20B:
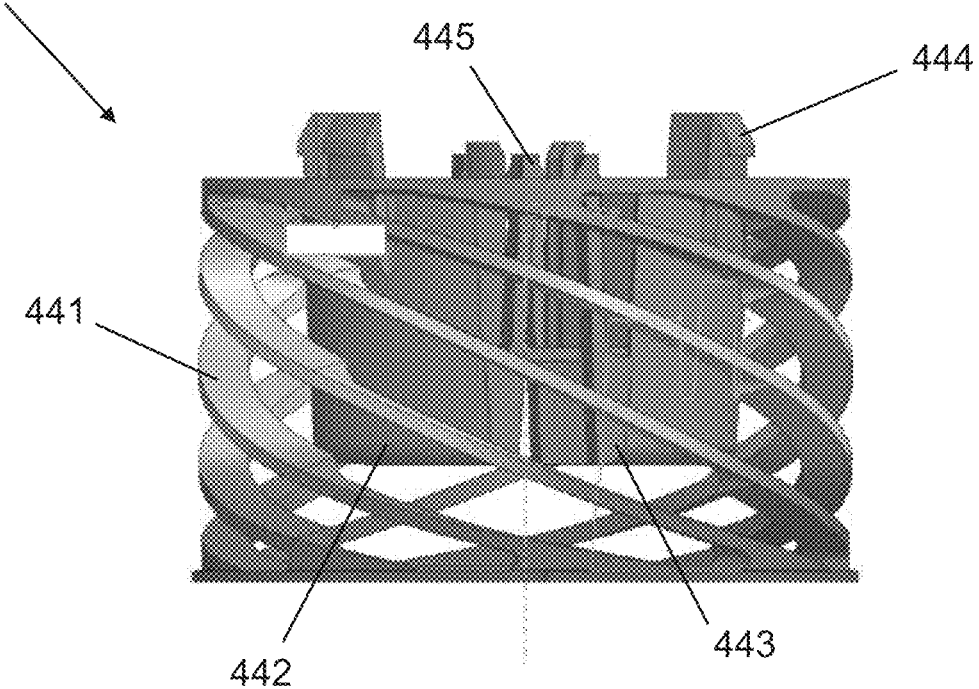
FIG. 20B shows the striker or plunger of FIG. 20A in a biased state.
Figures 21A, 21B:
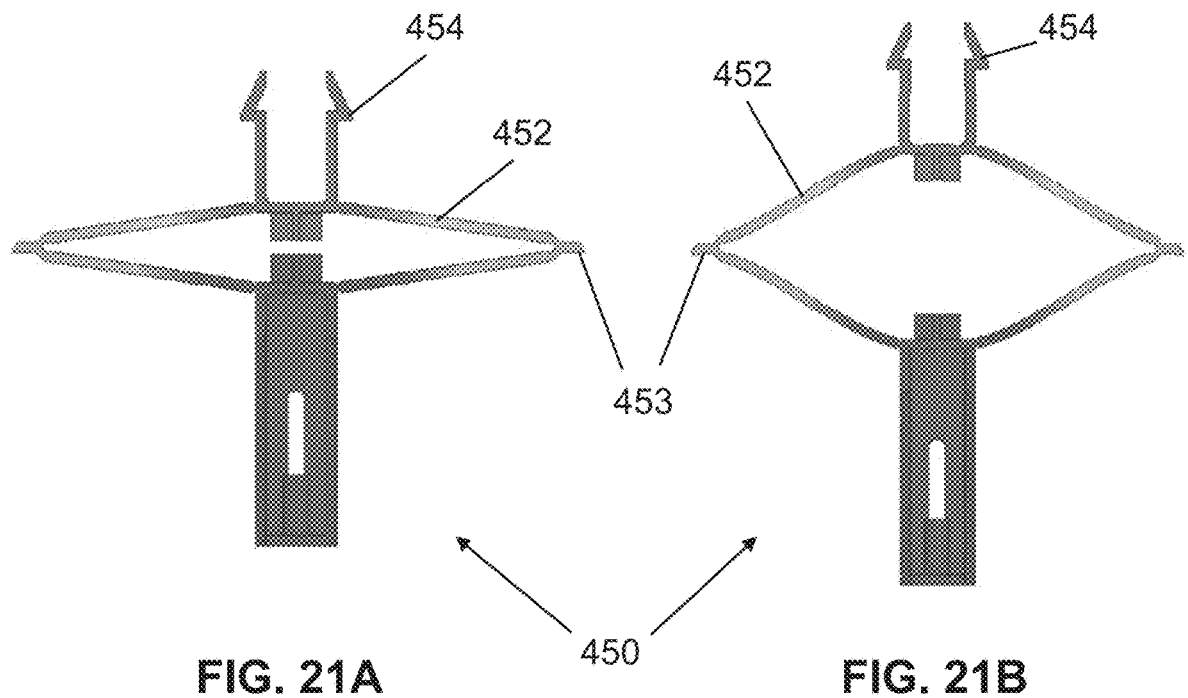
FIG. 21A shows a side view of a needle carrier of the applicator assembly in an unbiased state according to the fourth embodiment.
FIG. 21B shows the needle carrier of FIG. 21A in a biased state.

The plunger 440 is shown in greater detail in FIGS. 20A and 20B. The plunger 440 includes an outer spring 441 with a plurality of interconnected spring components. There are eight separate spring components in the embodiment shown, which are interconnected via a closed ring either on the top or the bottom of the plunger 440, or both. The components of the spring 441 can be molded, for example, injection molded. Other embodiments may further include more or less than eight spring components that work together to provide a spring force to the plunger. The plunger 440 further includes a bucket 442 that forms a main body of the plunger, and in which the needle carrier 450 is located inside the assembly. The plunger further includes one or more engagement portions 443 near a bottom of the plunger and positioned radially on an outside of the bucket 442. In addition, the plunger 440 further includes two sets of latches, latches 444 for engagement with the frame 410 to hold the plunger 440 in a biased or fully cocked position, and latches 445 for engagement with a portion of the needle carrier 450.

The needle carrier or needle hub 450 includes a main body configured to hold the needle (not shown), resilient arms 452 that extend radially outwardly from the main body, tabs 453 at the outer ends of the resilient arms 452, and one or more engagement snaps, a button, or other engagement structure 454 at the top of the needle carrier 450 to permanently attach to the frame 410. The resilient arms 452 are arranged such that the axial ends of the needle carrier 450 are urged back towards one another by the resilient arms 452 if they are pulled away from one another, for example, by outside forces. In other words, when the main body of the needle carrier is pulled away axially from the snaps 454, the resilient arms 452 are configured to urge the main body and the snaps back towards one another.

Figure 22:
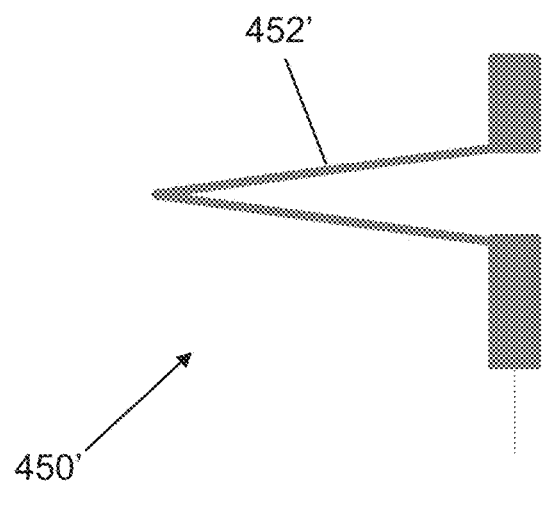
FIG. 22 shows a schematic view of a needle carrier according to an alternative embodiment.

FIG. 22 shows an alternative embodiment of a needle carrier or needle hub 450', where there is only one resilient arm 452' instead of two resilient arms. The single resilient arm 452 may be longer to provide sufficient force. For embodiments of applicator assemblies where an asymmetric variant of a needle carrier such as needle carrier 450' is utilized, the design of the entire applicator assembly may correspondingly be made asymmetrical to facilitate the asymmetric position of the needle in this arrangement, and needle deployment in such applicator assemblies may be off center relative to a central axis of the applicator assembly.

Referring back to FIGS. 18 to 19B, the applicator assembly 400 may initially be provided in a shipping state. In this embodiment, an additional overmolding 460 is provided on at least part of an outer surface of the frame 410. The overmolding 460 may be applied using a 2 k injection overmold on part of the frame 410, or other overmold methods may also be used. The overmold 460 may improve grip on the frame 410 when rotating the frame relative to the cap 430 and uncapping the assembly. In addition, the overmold 460 may also integrate low pressure wiper seals to provide for a sterile barrier with either the cap, the button, or both. Even with an overmold layer 460, other arrangements may also be used to provide and maintain sterility of the applicator assembly 400.

As shown in FIG. 19A, in the initial shipping state, the engagement portion 454 of the needle carrier 450 is snapped in or otherwise permanently fixed against a ledge 411 on the frame 410. The button may further include an engagement means that prevents the engagement portion 454 from disengaging from the ledge 411, for example, by blocking radially inward movement of the engagement portion 454. The resilient arms 452 of the needle carrier 450 are in an unbiased state, and the spring 441 of the plunger 440 is also in an unbiased state or in a slightly biased state, similarly as described with respect to the first embodiment. Here, the cap 430 may apply or otherwise contribute to the slight biasing of the spring 441 of the plunger 440.

In this embodiment, a cradle 2220 or other payload is shown, where the cradle 2220 is held at a bottom of the plunger 440 and captured or otherwise held in place between the cap 430 and the bottom of the plunger 440 and/or the bottom of the needle carrier 450. In this arrangement, the needle 451 may extend through the cradle 2220, with a sensor member housed at least partially inside the needle 451, such that upon deployment, the sensor member may be advanced together with the needle under a user's skin, and then may detach from the needle 451 and be left in a desired position under the patient's skin while the needle 451 is retracted and removed from the user's body.

Figure 23:
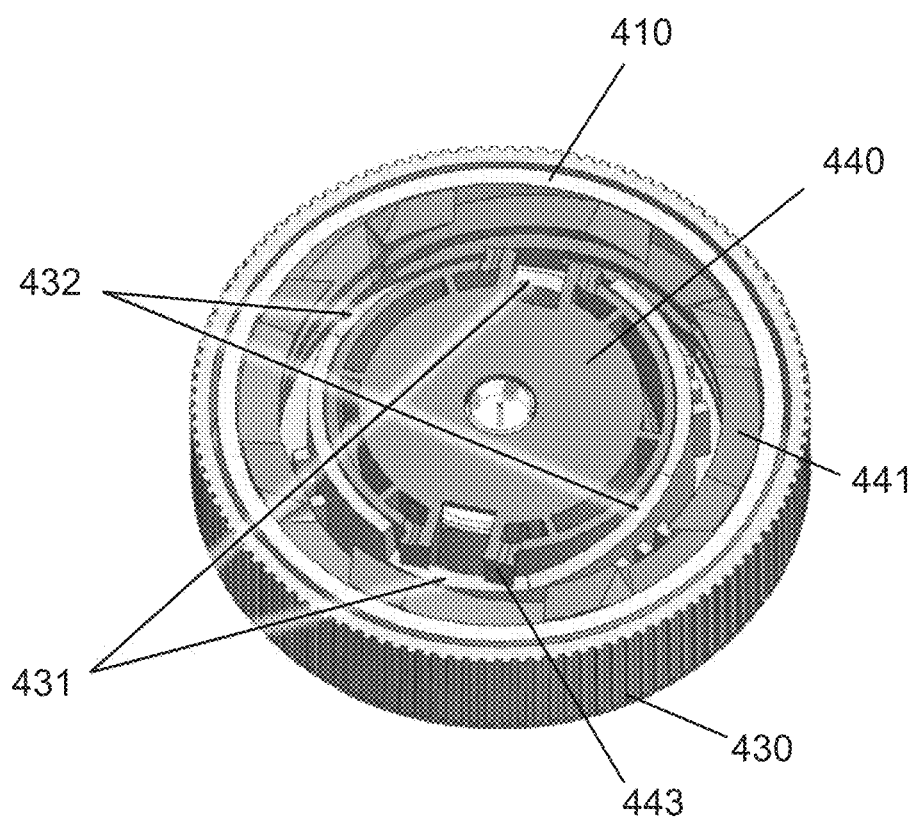
FIG. 23 shows a cross-sectional view of the applicator assembly according to the fourth embodiment in the shipping state, with the cross-section taken in a plane perpendicular to a longitudinal axis of the applicator assembly.

FIGS. 23 to 25B show sequential steps during cocking of the applicator assembly 400 according to the fourth embodiment. Similar to the first embodiment, the spring 441 of the plunger 440 may be cocked or otherwise biased via rotation of the cap 430 relative to the frame 410. The cross-sectional view of FIG. 23 shows shelves 431 and ramps 432 found on cap 430 that are arranged similarly to the shelves 131 and ramps 132 on the cap 130 in the first embodiment. However, in this embodiment, cap 430 only includes two shelves 431 and ramps 432, with the ramps 432 arranged in a helical manner, rather than the three shown in the first embodiment. However, other embodiments may include more or less shelves and/or ramps as necessary. In FIG. 23, the engagement portions 443 of the plunger 440 are resting on the shelves 431, so FIG. 23 shows an the arrangement of parts prior to rotation of the cap 430 relative to the frame 410.

Figures 24A, 25A:
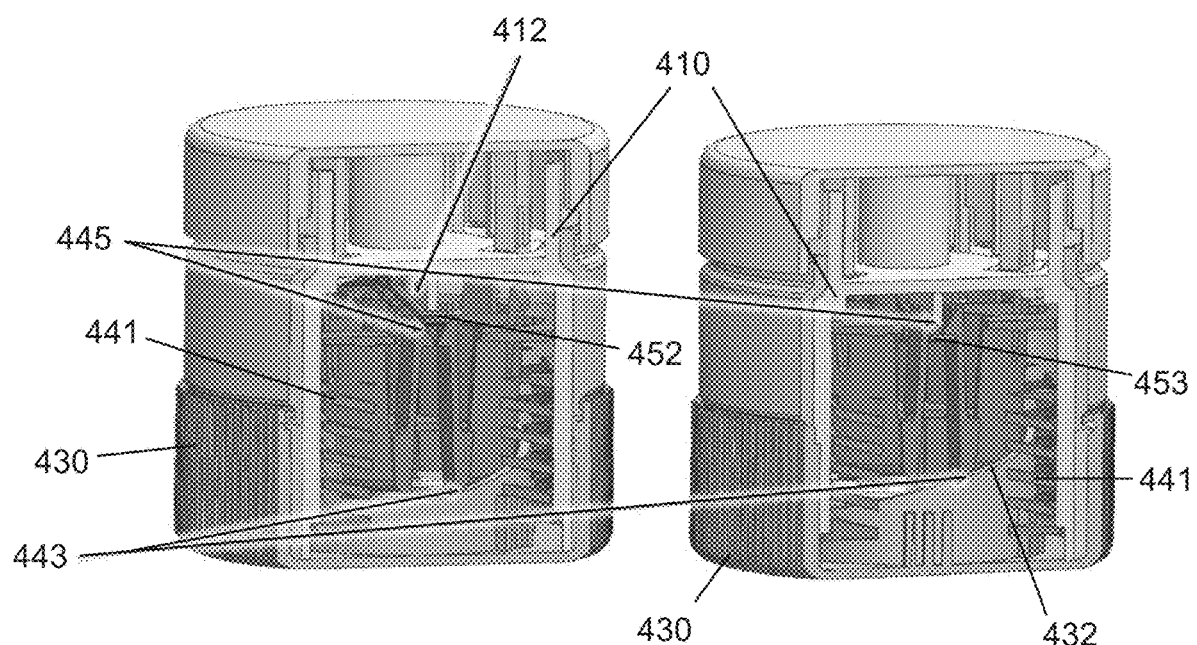
FIGS. 24A and 24B show cross-sectional views of the applicator assembly according to the fourth embodiment during a step of cocking or otherwise biasing the striker or plunger.
FIGS. 25A and 25B show cross-sectional views of the applicator assembly according to the fourth embodiment after fully cocking or otherwise biasing the striker or plunger.
Figures 24B, 25B:
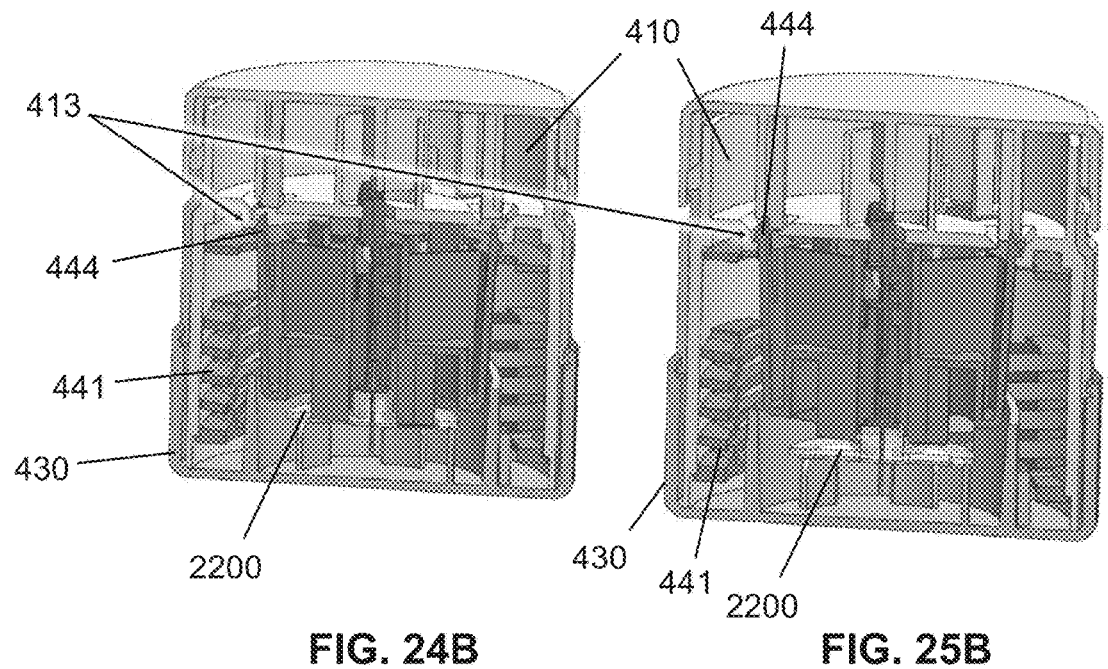
Figure 26:
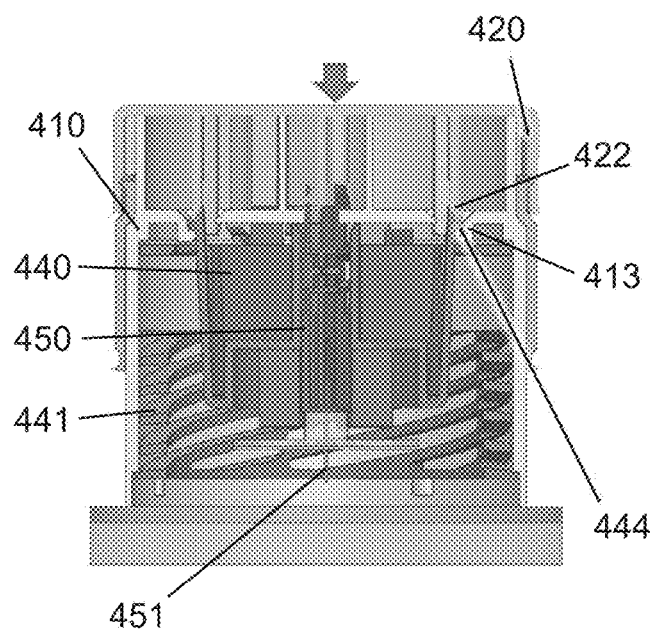
FIG. 26 shows a cross-sectional view of the applicator assembly according to the fourth embodiment with the striker or plunger in a biased state, with a cap of the applicator assembly removed and with a button of the applicator assembly being depressed.

FIGS. 24A and 24B show an intermediate step during cocking of the applicator assembly 400 via rotation of the cap 430 relative to the frame 410. During rotation of cap 430, a bottom of the spring 441 of the plunger 440 is held or constrained against upward movement, for example, by a ledge on the frame 410 snapping against, abutting against, or otherwise engaging an outer flange of the plunger 440. The constraints may further be orientation keyed to restrict unwanted rotational movement between the plunger 440 and the frame 410. Meanwhile, the engagement portions 443 on the plunger 440 are translated upward along ramps 432 of cap 430, such that bucket 442 is moved upwards relative to the frame 410 and the spring 441 is biased or otherwise tensioned via stretching out vertically. This energy stored in the spring 441 will provide sufficient energy for firing later. During this movement, the resilient arms 452 of needle carrier 450 abut against a projection 412 on the frame, to prevent unwanted shifting or other movement of the needle carrier 450 relative to the rest of the applicator assembly 400.

Rotation of cap 430 continues until the fully cocked configuration shown in FIGS. 25A and 25B. In the fully cocked state, latches 444 on the plunger 440 will snap past ledges 413 on the frame 410 to hold the plunger 440 in the loaded or fully cocked state with the springs 441 held in the biased condition. Furthermore, latches 445 on the plunger 440 will snap past tabs 453 on the needle carrier 450, so that downward movement of the plunger 440 during firing of the applicator assembly 400 later will translate into corresponding downward movement of the needle carrier 450 as well. The tabs 453 of the needle carrier 450 are held axially against upward movement by the projection 412 of the frame 410, to facilitate passing of the latches 445 of the plunger 440 over them. In the embodiment shown, the plunger 440 includes four latches 444 that may be grouped into pairs, or alternatively positioned equidistantly from one another, around a circumference of the plunger 440, but other embodiments may include more or less latches 444 arranged in similar or different manners. The plunger 440 further includes four latches 445 provided in the form of tab snaps that snap against the tabs 453 of the needle carrier 450. The tab snaps 445 are grouped into pairs, with two tab snaps 445 configured to engage each of the tabs 453. Other embodiments may include more or less tab snaps as needed. The height and inclination of the ramps 432 in different embodiments can be adjusted based on the structure of the springs 441 of the plunger 440, in order to facilitate sufficient cocking and proper engagement and holding at the fully cocked state. The height of the ramps 432 should be selected to be substantially equivalent to the cocking distance plus the thread lead times the percentage of a full rotation of cap 430 around the central axis of the applicator assembly 400 necessary to fully cock the device and disengage the cap 430.

In this embodiment, it has been observed that the plunger 440 or just the spring 441 may tend to rotate during the cocking or loading process. Further improvements will consider whether it is more beneficial to account for and potentially take advantage of any such rotational movement, or to constrain it instead.

Figure 27:
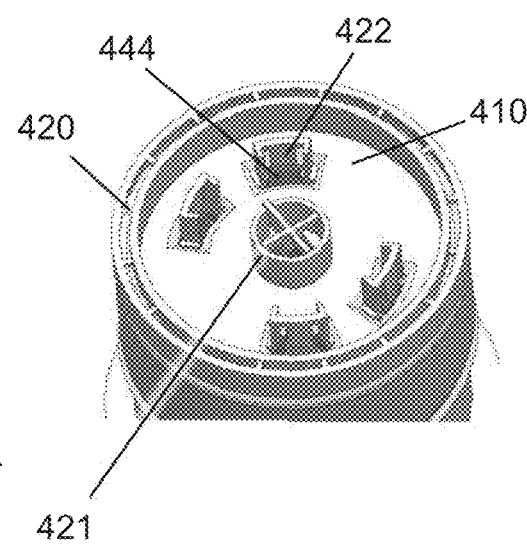
FIG. 27 shows a cross-sectional view of the applicator assembly according to the fourth embodiment in the state shown in FIG. 26, with the cross-section taken in a plane perpendicular to the longitudinal axis of the applicator assembly.
Figure 28A:
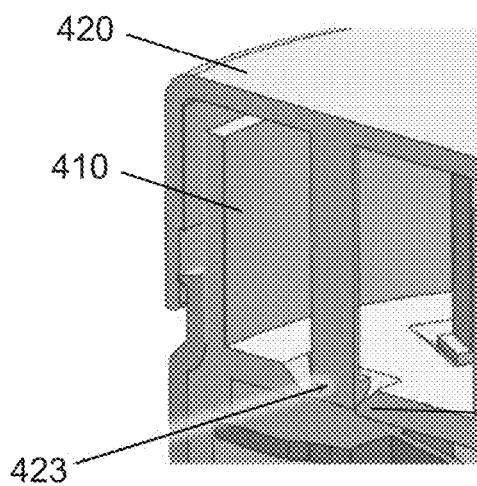
FIGS. 28A and 28B show cross-sectional views of a close-up of the button interacting with a frame of the applicator assembly according to the fourth embodiment when the button is depressed.
Figure 28B:
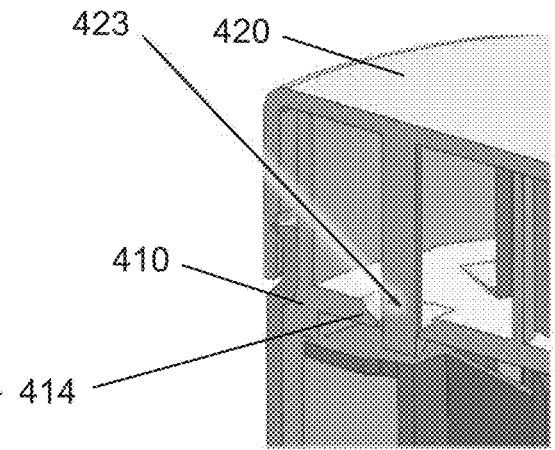

FIGS. 26 to 28B show steps of firing or actuating the applicator assembly 400 according to the fourth embodiment. When ready, a user can depress the button 420 to fire the applicator assembly 400. The respective lengths and clearances of the button 420 relative to the frame can be selected in order to provide a tight clearance fit between the respective parts to ensure a straight button press and, for example, disengagement of all of the latches around the circumference of the device. Furthermore, a connection 421 between the button and the frame can be keyed to ensure a desired rotational orientation between the respective parts. Upon depression of the button 420, projections 422 push or otherwise urge latches 444 of plunger 440 radially inwardly to disengage the latches 444 from the ledges 413 of frame 410. This action releases or disengages the plunger 440 from the cocked position, and the spring 441 is allowed to start pulling the bucket 442 downwards towards the user's skin. Additionally, latches 423 on the button are configured to engage ledges 414 on the frame to hold the button 420 in the depressed state and to provide an audio or tactile click feedback, or both, to ensure that the button 420 has been fully depressed. On the other hand, ramps on these features may provide resistance against unintended firing, such that an additional amount of force is necessary to get the respective latches past the ramps and into final engagement. Lastly, in some embodiments, the latches 423 may be formed on or otherwise integrated with projections 422, such that the same ledges on the frame 410 can be utilized for engaging both the latches 444 of the plunger and the latches 423 of the button 420, as best seen in FIG. 27.

Sequential progression of firing and needle retraction according to the fourth embodiment are further shown in FIGS. 29A to 29D. First, as shown in FIG. 29A, as the spring 441 fires down and urges the bucket 442 downward, the tab snaps 445 of the plunger 440 that engaged the tabs 453 of the needle carrier 450 during cocking, push down on the tabs 453 and deflect the entire beam of the resilient arms 452 downward, along with the needle 451. The beam structure of the needle carrier 450 further accelerates the wearable device or other payload 2220 down towards the surface of the user's skin. Due to the shape of the resilient arms 452, downward movement and axial expansion of the resilient arms 452 also result in radial compression of the arms 452, causing the tabs to start to move radially inwardly as well as the tabs 453 are pushed down, as shown in FIG. 29B. When the needle 451 reaches the full desired depth in the user's body, the payload 2220 will also have been pushed against and adhered to the user's skin. Here, the tabs 453 of the needle carrier 450 have moved radially inwardly a sufficient amount to start to slip past the undercuts of the tab snaps 445 on a radially inside thereof. As shown in FIG. 29C, the tab snaps 445 of the plunger 440 then begin to travel downwardly past the tabs 453 of the needle carrier 450, allowing the tabs 453 to move upwardly past the tab snaps 445. Here, the payload 2220 will stay in place on the user's skin even though the needle carrier 450 begins pulling away therefrom. Then, as shown in FIG. 29D, the resiliency of the resilient arms 452 forces the main body of the needle carrier 450, along with the needle 451, to retract upwardly and snap back into the applicator assembly 400. In a fully retracted position, the payload 2220, for example, a cradle of a continuous glucose monitor, has been properly adhered to the surface of a user's skin, while a sensor monitor 2230 has been properly positioned in under the user's skin. Meanwhile, the needle carrier 450 has pulled the needle 451 sufficiently back up so that the entire needle has detached from the payload 2220 and is safely contained inside the profile of the applicator assembly 400, for example, where a tip of the needle 451 is axially recessed from an end face of the plunger 440.

Figure 30A:
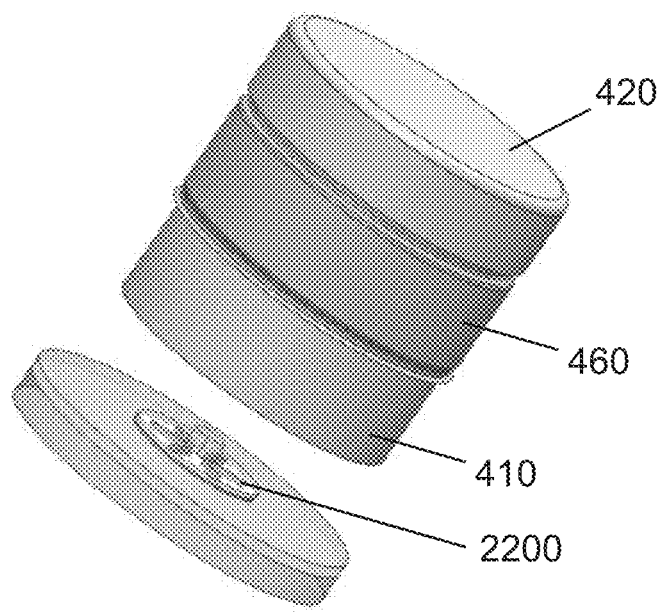
FIG. 30A shows a perspective view from above of the applicator assembly according to the fourth embodiment being separated from a patient's body after actuation.
Figure 30B:
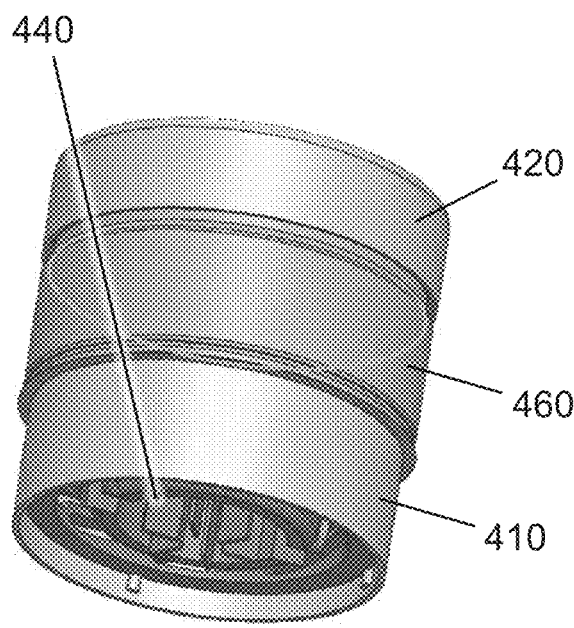
FIG. 30B shows a perspective view from below of the applicator assembly shown in FIG. 30A.

Thereafter, as shown in FIGS. 30A and 30B, the applicator assembly 400 can be removed from the surface of the user's skin, while the payload 2220 remains in place thereon, with the sensor member 2230 properly implanted under the user's skin. Here, ribs or other features on a bottom surface of the plunger 440 may further serve to guard the needle at the end of travel. In some embodiments, after snap back, there may be one or more additional snaps to keep either the plunger 440, the needle carrier 450, or both, in a safe position relative to the rest of the applicator assembly 400.

As noted above, in some embodiments, the needle and sensor may be inserted at an angle relative to the surface of the patient's skin. FIGS. 31A to 31D show an applicator assembly 500 according to a fifth embodiment. The illustrations in FIGS. 31A to 31D schematically show internal components of the applicator assembly 500 in cross-sectional view, and may omit some components for simplicity, such as a button for firing the applicator assembly.

In the embodiment in FIGS. 31A to 31D, the device is capable of angled insertion of a sensor member and/or longer strokes. Some actual implementations of applicator assemblies may use this or a similar asymmetric configuration, rather than one of the previously discussed symmetric rivet designs. The mechanism provided in the fifth embodiment in FIGS. 31A to 31D is otherwise similar to the fourth embodiment discussed above. The applicator assembly 500 includes at least a main body or frame 510, a button or other actuator (not shown), a striker or plunger 540, and a needle carrier 550 with a needle 551. The applicator assembly 500 may further hold a wearable device or other payload 2300. The plunger includes a spring 541 and a tab snap 545, while the needle carrier 550 includes a single asymmetric resilient arm 552 with an end tab 553. The long living hinge beam of the resilient arm 552 may have an accelerating effect compared to previously discussed designs due to increased leverage during firing. The spring 541 of the plunger 540 will pull the tab 553 down at a first velocity, but the increased length of the resilient arms will cause the end of the needle carrier 550 holding the needle 551 to move a greater distance in the same time, making the needle move at a higher second velocity, with the differential between the first and second velocities dependent on the length of the beams of the resilient arm 552 and other factors.

Figure 31A:
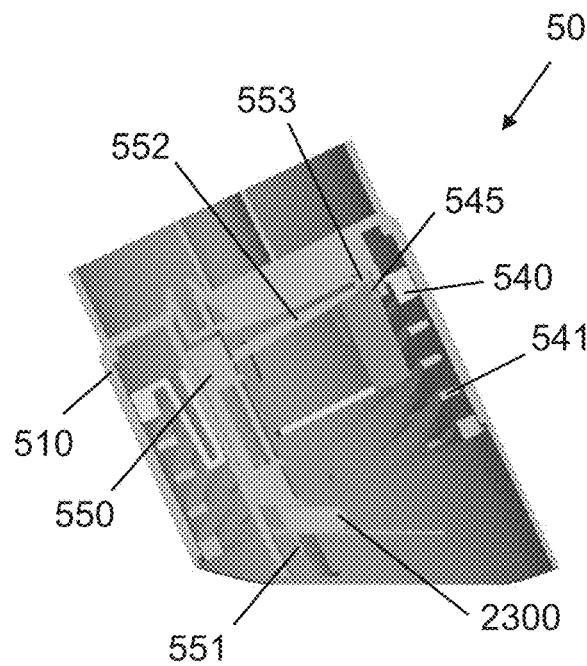
FIGS. 31A to 31D show cross-sectional views of steps of operating an applicator assembly according to a fifth embodiment.
Figure 31B:
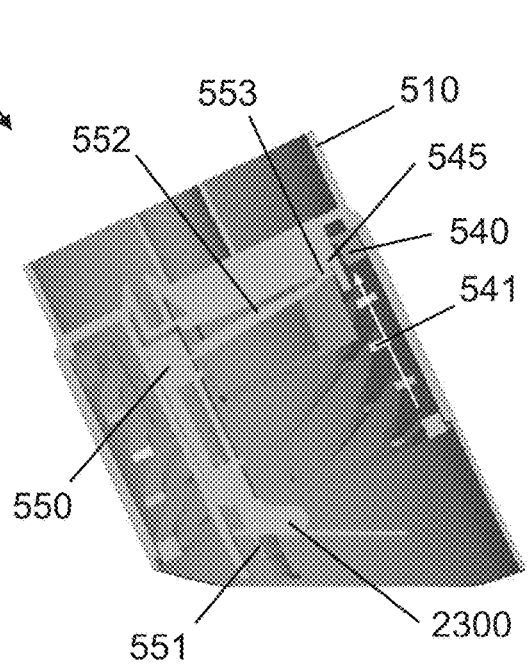
Figure 31C:
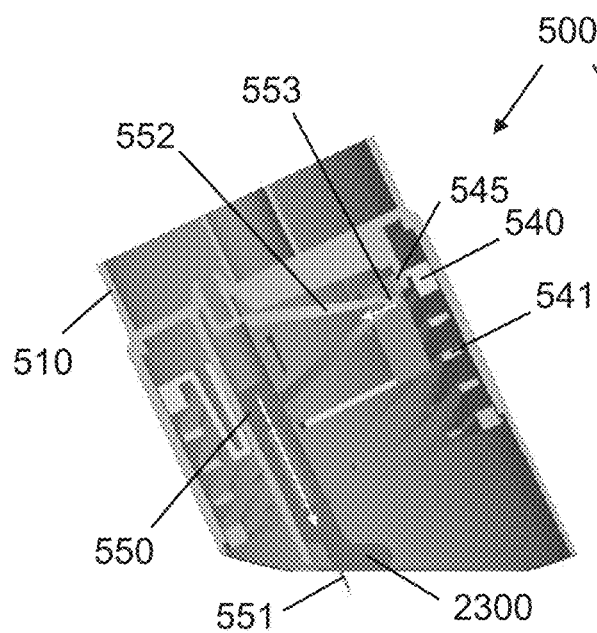
Figure 31D:
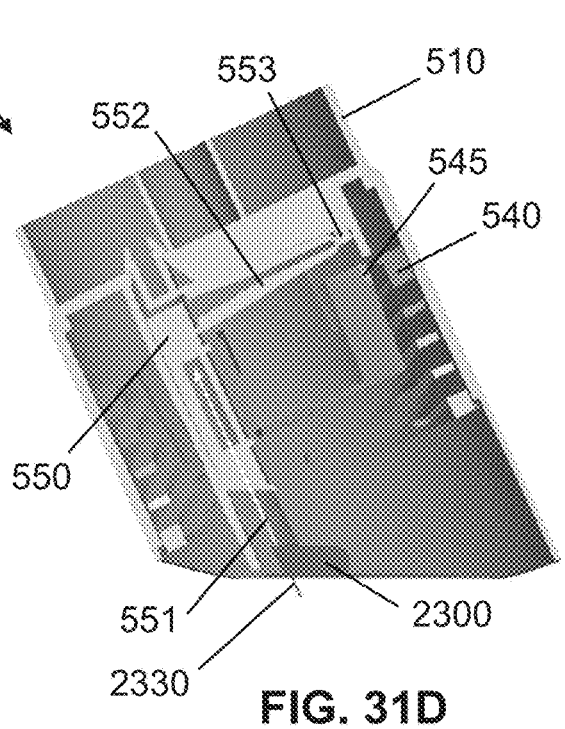

In a shipping state as shown in FIG. 31A, the needle carrier 550 is in an unbiased state, where the needle 551 may be positioned at an uppermost position. Meanwhile, the tab snap 545 of the plunger 540 has not yet engaged the tab 553 of the needle carrier 550. Upon loading or cocking of the spring 541, the top of the spring 541 is pulled upwards while the bottom of the spring 541 is held in place, in order to bias the spring 541. In addition, the spring is loaded upwards to a held position where the tab snap 545 of the plunger 540 moves past and snaps over the tab 553 of the needle carrier 550, as shown in FIG. 31B. Then, as shown in FIG. 31C, upon firing, for example, via depression of a button or similar actuator, the top of the spring 441 is released, which moves the body of the plunger 440 downwards towards the user's skin. This, in turn, causes the tab snap 545 of the plunger 540 to push down on the tab 553 of the needle carrier 550, so that the needle 551 and the payload 2300 are both pushed down towards the user's skin, until a final deployed position is reached where the payload 2300 is adhered to the user's skin, while the needle 551 has pierced through the skin to a desired depth. Here, in addition to stretching out axially, the resilient arm 552 of the needle carrier also moves radially inwardly, causing the tab 553 to move radially away from the tab snap 545 until their respective surfaces disengage. Upon disengagement between the tab 553 and the tab snap 545, the tab snap 545 continues to move together with the body of the plunger 540 towards the surface of the user's skin, while the resilient arm 552 pulls the tab 553, along with the needle 551, back into the frame 510 of the applicator assembly 500, where the needle can be safely housed after deployment.

An applicator assembly 600 according to a sixth embodiment is shown in FIGS. 32A to 32D. The applicator assembly 600 is similar to the applicator assembly 500 shown in FIGS. 31A to 31D, with a couple of significant differences. The applicator assembly 600 also includes a frame 610, a button or other actuator (not shown), a plunger 640 with a spring 641, and a needle carrier 650 with a needle 651 and a resilient arm 652.

The applicator assembly 600 according to the sixth embodiment differs from the applicator assembly 500 of the fifth embodiment first by the engagement between the tab 653 of the needle carrier 650 and the tab snap or catch 645 of the plunger 640. Here, the axial movement of the spring 641 of the plunger 640 further results in a rotational movement of the spring 641 relative to the rest of the device. Rotation of the spring 441 also causes rotational movement of the tab snap 645. Therefore, when the spring 441 is released, the resulting movement of the tab snap 645 includes both an axial component and a rotational component, where the rotation of the tab snap 645 is what causes disengagement with the tab at a desired depth. Taking advantage of the rotation of the spring 441 for disengagement between the respective parts results in lower stress on the parts and the potential for longer insertion strokes.

Figure 32A:
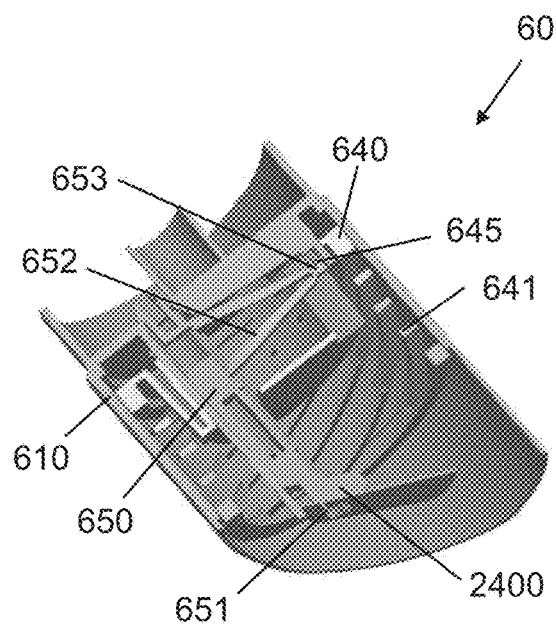
FIGS. 32A to 32D show cross-sectional views of steps of operating an applicator assembly according to a sixth embodiment.
Figure 32B:
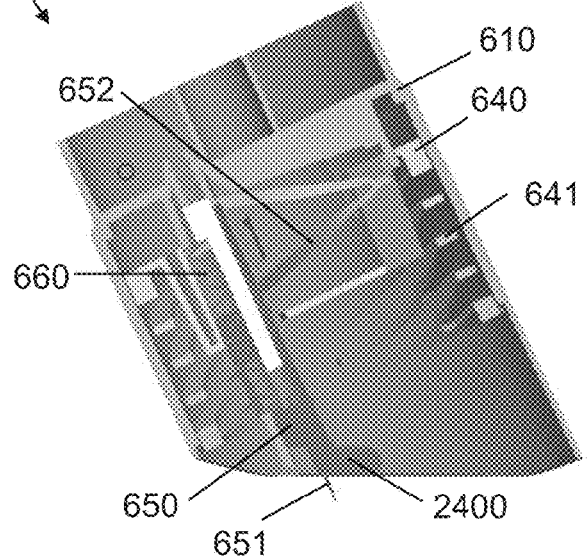
Figure 32C:
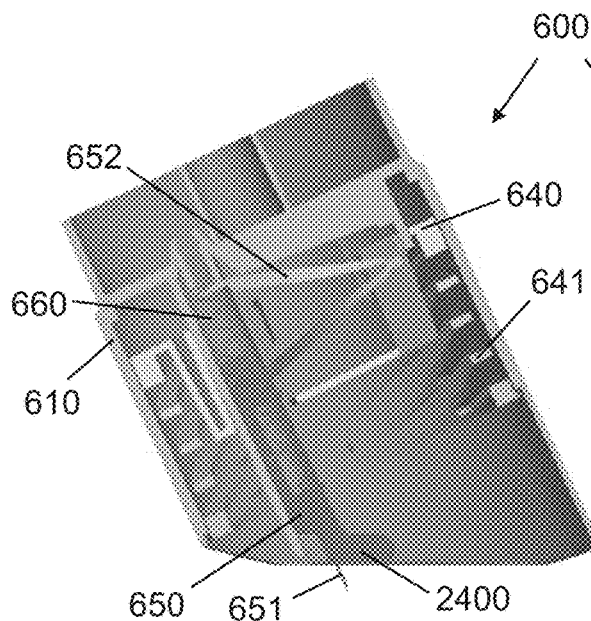
Figure 32D:
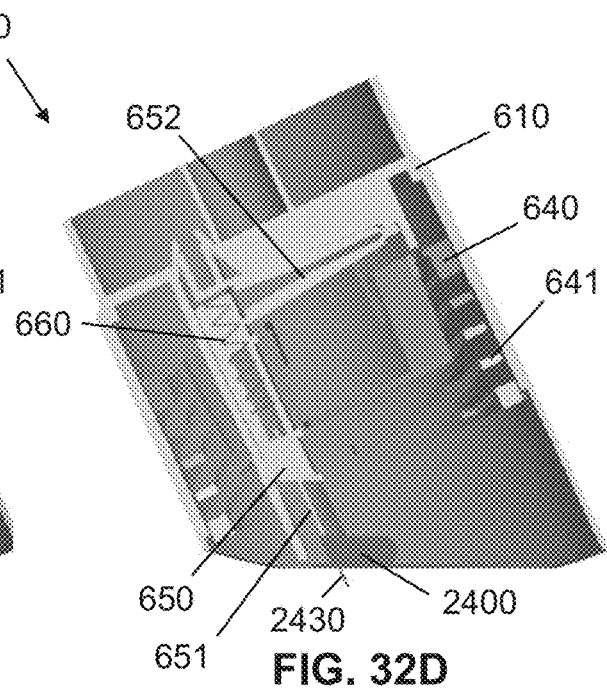

The second main difference of the applicator assembly 600 is the addition of a support spring 660 to the assembly. The additional support spring 660 may be a metal tension spring, or may also be molded, and is intended to aid in retraction of the needle carrier 650 if the plastic living hinge plastically deforms, either during storage or during firing and expansion, or is otherwise damaged or retracts more slowly than desired, for example, due to internal dampening of the material. Therefore, during firing as shown in FIGS. 32B and 32C, the support spring 660 is expanded together with resilient arm 652, and then during retraction, the support spring 660 works together with the resilient arm 652 to pull the needle 651 back into the applicator assembly 600 after firing and proper placement of the sensor member 2430 and the rest of the payload 2400.

Figure 33A:
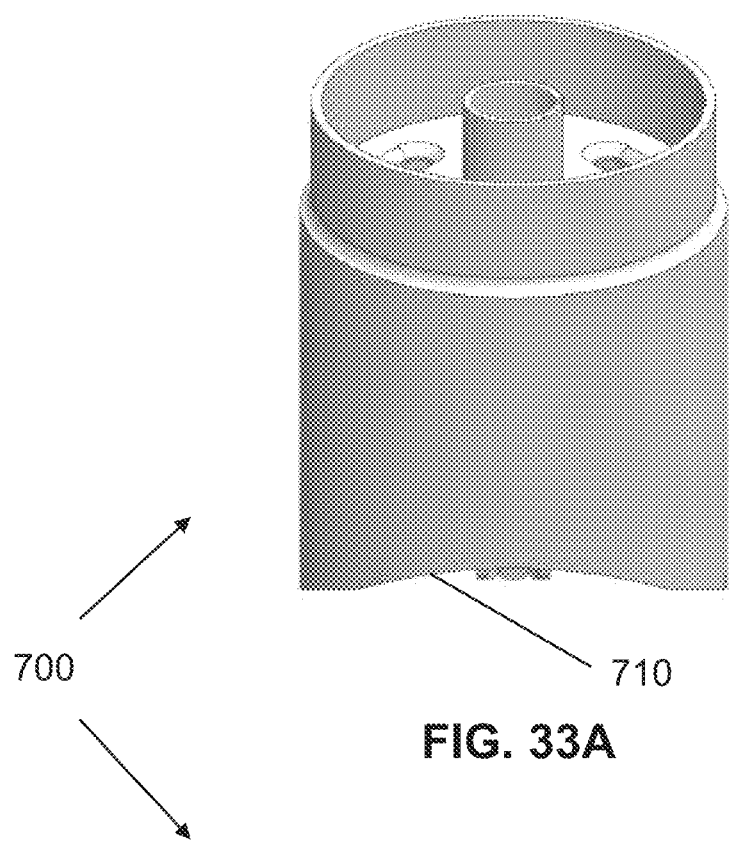
FIGS. 33A and 33B show perspective views of an applicator assembly according to a seventh embodiment.
Figure 33B:
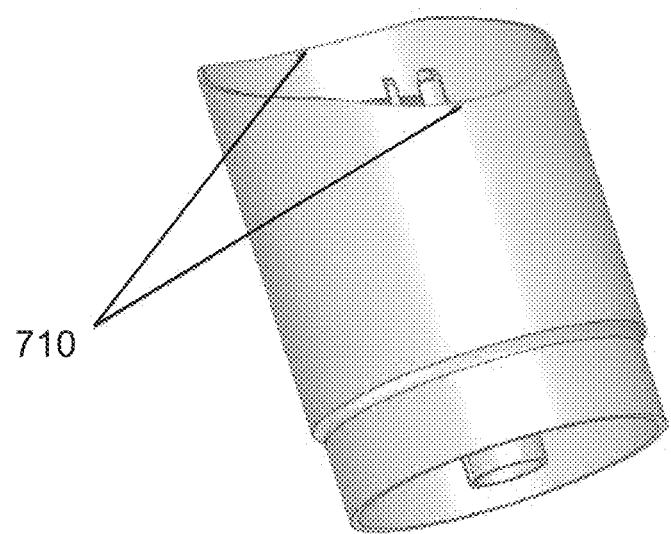

The seventh embodiment of the applicator assembly 700 shown in FIGS. 33A and 33B shows a modification where a bottom of the applicator includes cutouts 710 that make the bottom of the applicator assembly 700 non-planar. The cutouts 710 may be in the form of a concave channel which can be more easily contoured to a rounded surface such as a user's arm. Particularly for angled applicator assemblies, such a cutout 710 may be advantageous since it provides tactile feedback to aid in blind alignment and placement of the applicator assembly 700, for example, on the back of the user's arm. The channel 710 arranged from front to back on the bottom of the frame of the applicator assembly 700 may further assist in aligning the applicator so that the insertion direction is roughly aligned with the longitudinal extension of the arm, which may further be beneficial in some applications.

Figure 34:
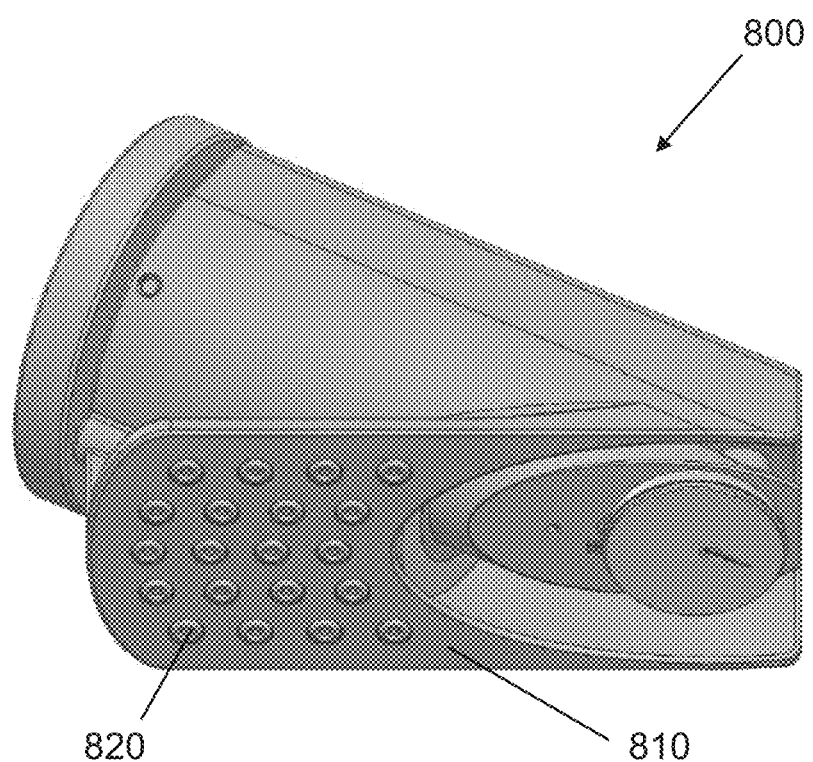
FIG. 34 shows a perspective view of an applicator assembly according to an eighth embodiment.

The eighth embodiment of the applicator assembly 800 shown in FIG. 34 includes a bottom engagement surface 810 configured to rest on the user's skin. The bottom engagement surface 810 further includes one or more high friction elements 820, such as added texture or beads made of high friction material, so that when held firmly against the user's skin, the applicator assembly 800 can be held in place more steadily and not slide around. This may improve usability of applicator assemblies with steep insertion angles, where a force from firing may tend to shift the applicator assembly during application of a given payload. Other friction elements and/or mechanisms can also be implemented in other embodiments with similar results.

In one embodiment, the high friction surface 810 may assist in pulling the skin at the insertion site taut or bunch the skin up as the user slides the applicator assembly as part of an applicator process or workflow. In another embodiment, the user can slide the applicator and create tension at the high friction surface that can overcome a spring force to release the actuator and deploy the sensor, for example, in lieu of the buttons previously discussed in earlier embodiments. Other implementations of high friction surfaces may also be utilized in still other embodiments.

A sensor 1000 according to a first embodiment is shown in FIGS. 35A to 37B, and is configured for use with applicator assemblies according to the various embodiments of the invention. The sensor 1000 includes a main body 1010 and a sensor member 1020, that is, an implantable portion of the sensor 1000. The implantable sensor member 1020 includes an end 1021 and a neck 1022, with sensing electrodes 1030 located near the end 1021 of the sensor member 1020. The electrodes are connected to contacts 1040 at an opposite side of the main body 1010 via circuitry 1050 that extends through the sensor 1000. The electrodes 1030, contacts 1040, and circuitry 1050 may all be printed or otherwise formed. The contacts 1050 may electrically connect the electrodes 1030 to other components in the monitor, for example, a processor and/or a transmitter.

FIG. 35B shows a close-up of the electrodes 1030 of sensor 1000. The electrodes are arranged close together near an end 1021 of the sensor member 1020, so that they can all be located in a same tissue space upon insertion under a patient's skin. Electrodes that are arranged parallel to one another as shown ensures that they will be located in the same tissue space. In contrast, stacked electrodes risk having different electrodes located in different tissue space after insertion, which would create inaccurate data based on different glucose concentration levels in different tissue layers.

As illustrated in FIG. 36, in some embodiments, insertion of the sensor member 1020 under the patient's skin may be performed at an angle, and in particular, may be near parallel to the skin of the patient. A flat sensor member 1020 and correspondingly flat electrode 1030 may facilitate such insertion. A steep angle of insertion allows electrodes to be less than 40° from parallel with the skin. This may provide for several benefits. For example, larger electrodes are easier to locate in the dermis, which is a relatively shallow layer of the skin. Furthermore, if arranged at an angle, electrodes that are longer than the dermal layer can be used, maximizing signal and minimizing width of the sensor, which can allow for a smaller needle. A narrower sensor member 1020 also makes it easier to insert the sensor member 1020 into a correct or desired space. 40° angulation or less is only presented as an example, and other embodiments may include implantation at different angles.

Figure 37A:
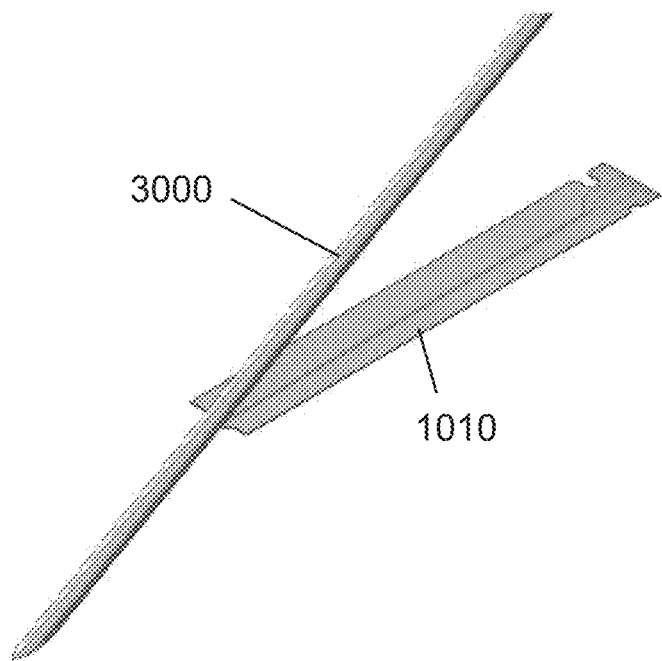
FIGS. 37A and 37B show perspective views of the sensor of FIGS. 35A to 36 loaded on a needle according to the first embodiment.
Figure 37B:
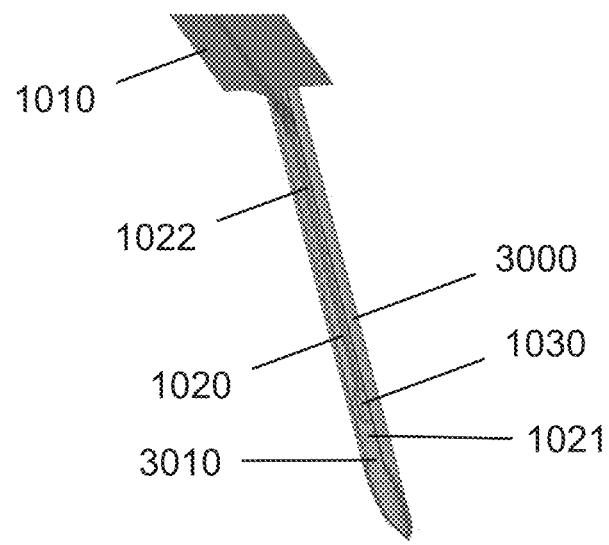

Referring back to FIG. 35A, in the embodiment shown, the neck 1022 of the sensor member 1020 further has a reduced width, particularly in comparison to the wider end 1021 of the sensor member 1020. The narrow neck 1022 of the sensor member 1020 may improve sensor retention in the skin, as the wider end 1021 may be more difficult to dislodge after implantation. In addition, as best seen in FIG. 37B, the narrow neck 1022 of the sensor member 1020 allows the neck 1022 to fit out of or pass through a longitudinal slot 3010 on the needle 3000 when the sensor member 1020 is loaded onto the needle 3000, while the enlarged end 1021 may not be able to fit through the slot 3010 of the needle 3000. This allows retention of the entire sensor member 1020 in the needle 3000 prior to deployment, and thereafter allows the sensor member 1020 to exit out of the distal end of the needle 3000 after the sensor member 1020 has been placed under the user's skin and the needle 3000 is retracted.

As can also be seen in FIG. 37B, the electrodes 1030 of the sensor 1000 may be arranged to be face down, as can the bevel and slot 3010 of the needle 3000. Having a needle 3000 with the slot 3010 face down allows for a more gentle bend in the sensor member 1020 when inserting the sensor member 1020 at a steep angle. Furthermore, arranging the electrodes 1030 of the sensor member 1020 face down may allow the electrodes 1030 to be positioned in a more desired or intended tissue space, among other benefits. In other embodiments, it may be beneficial to arrange the electrodes 1030 of the sensor member 1020 face up instead, so long as the desired orientation allows a user to more accurately position the electrodes 1030 in the most desired or proper tissue space for accurate readings and/or data collection.

FIGS. 38 to 43B show various different embodiments of implantable portions of sensor members and various engagements with modified needles that may improve dermal penetration and/or detachment of the sensors after insertion under a patient's skin. These various designs may serve to pull the sensor members towards their final locations rather than pushing the sensor members, and therefore may further help maintain tension on the various sensor members during insertion, so that the sensor members do not bunch up when they or the needles hit the skin or during advancement before or after. In addition, in embodiments with a set engagement region on the sensor members, the arrangements may further lift other portions of the sensor members away from the surface of the needle and reduce friction during retraction of the needle.

FIG. 38 shows a sensor member 1120 that is a modified version of the first embodiment of the sensor member 1020 shown in FIGS. 35A to 37B, where the sensor member 1120 according to the second embodiment also includes a wider end portion. The end portion can include a fold or crease 1124, to provide additional stiffness to the sensor member 1120, and in some embodiments, the fold or crease may also facilitate easier insertion into a slot of a needle during insertion or implantation.

FIG. 39 shows a sensor member 1220 according to a second embodiment. The sensor member 1220 includes an enclosed hole 1225 at or near an end of the sensor member 1220. A modified needle 3200 includes a slot 3210 and a bent tang 3220 that is configured to extend through and engage the hole 1225 of the sensor member 1220. The tang 3220 is open distally, and acts like a uni-directional hook, that is configured to pull the sensor member 1220 during advancement to a desired position under the patient's skin, but can then be disengaged easily when the needle 3200 is pulled back out of the patient, leaving the sensor member 1220 at the desired position.

FIG. 40 shows a sensor member 1320 according to a third embodiment. The sensor member 1320 is similar to the sensor member 1220 according to the second embodiment, but instead of a closed hole 1225, the sensor member 1320 includes a J-hook 1325, that is configured to engage a similar tang 3320 on the slot 3310 of a needle 3300. The J-hook 1325 may in some instances be easier or cheaper to manufacture than a closed hole.

FIG. 41 shows a sensor member 1420 according to a fourth embodiment. The sensor member 1420 includes a folded tip 1425 that is configured to engage an open slot 3420 at an end of a modified needle 3400. The folded tip design would not require a hole or cutout in the sensor member 1420, thereby reducing potential damage or weak points on the sensor member 1420, and also would not require a bent tang or other hook feature to be additional manufactured on the needle 3400. A sensor member 1520 according to a fifth embodiment is similar to the sensor member 1420 according to the fourth embodiment, but in addition to a folded tip 1525 configured to engage an open slot 3520 at an end of a further modified needle 3500, the sensor member 1520 further includes a second fold or extension 1526 configured to engage a second slot 3530 on the needle 3500 to further enhance a hold between the sensor member 1520 and the needle 3500 during insertion.

A sensor member 1620 according to a sixth embodiment includes a closed hole 1625 near an end of the sensor member 1620, similar to the sensor member 1220 shown in FIG. 39. However, instead of an internal tang or hook, the tip 3620 of the needle 3600 is simply threaded through the hole 1625 to hold the sensor member 1620 against the needle 3600. In this embodiment, the tip 3620 of the needle 3600 may be further modified to more effectively engage the hole 1625 of the sensor member 1620, for example, side cutouts that form a more straight or smooth abutment against which the sides of the sensor member 1620 can rest, and to reduce potential rupture of the portions of the sensor member 1620 around the hole 1625.

Further modifications to both applicator assemblies and monitors can also be made without departing from the scope of the invention.

Figure 44A:
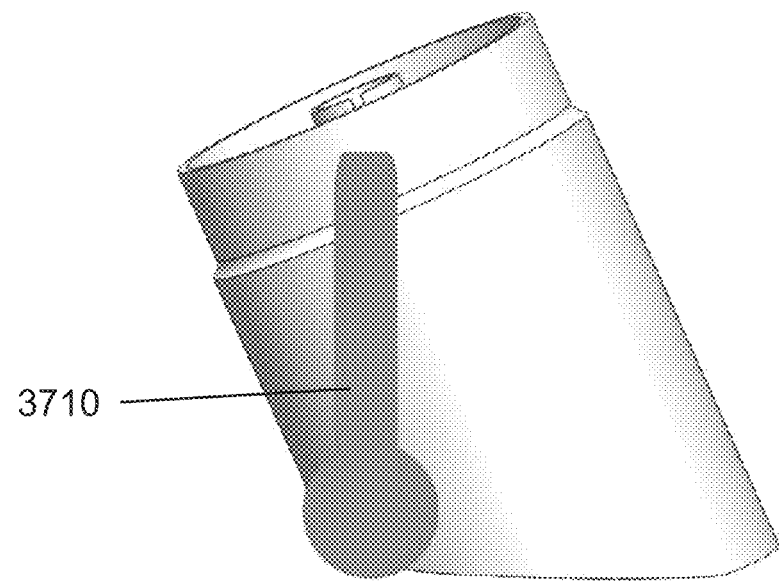
FIG. 44A shows a perspective view of an applicator assembly according to a further embodiment.
Figure 44B:
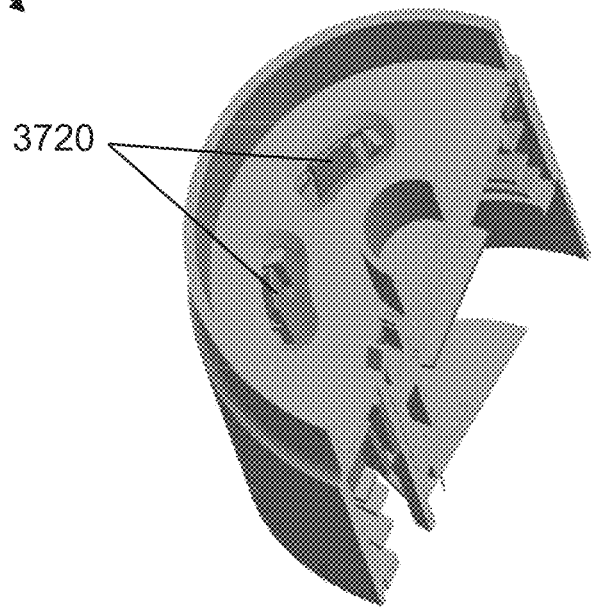
FIG. 44B shows a cross-sectional view of the applicator assembly of FIG. 44A from a top perspective angle.
Figure 45A:
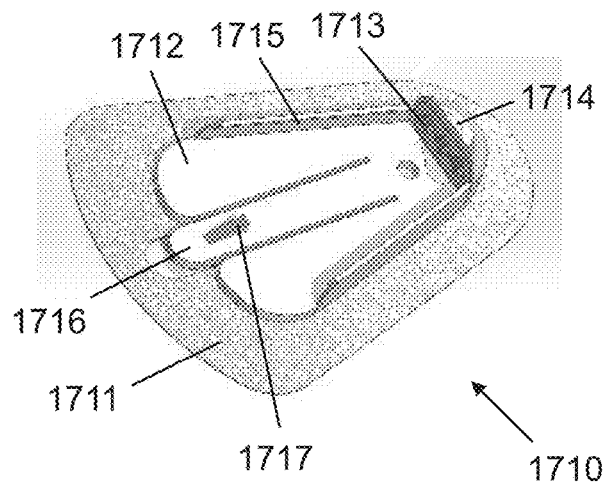
FIGS. 45A and 45B show perspective views of a cradle of a monitor according to a seventh embodiment.
Figure 45B:
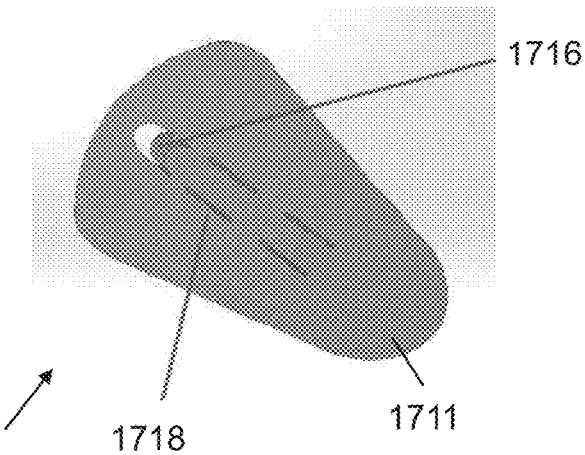
Figure 45C:
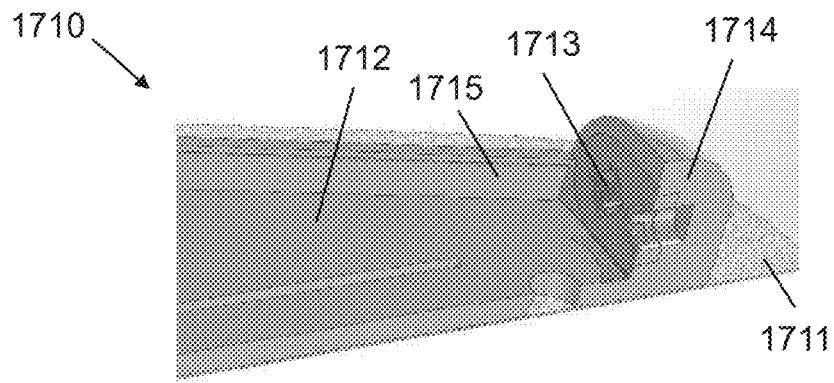
FIG. 45C shows a cutaway perspective view of the cradle of FIGS. 45A and 45B.

For example, FIGS. 44A and 44B provide yet another modification to applicator assembly that could reduce occurrences of misfires. The applicator assembly 3700 according to yet another embodiment includes two separate triggers 3710 (schematically shown) for dual trigger firing, where a user may be required to actuate both triggers in order for firing of the applicator assembly 3700 to occur. In these embodiments, there may be two separately controlled latches 3720, which both need to be released via the separate triggers 3710, in order to activate the applicator assembly 3700. As can be imagined via the schematic triggers 3710 shown in FIG. 44a, the enlarged bottoms of the triggers may represent buttons or pressing surfaces, while the vertically extending portions may be hinged beams or other mechanism that translates force to the latches 3720 in FIG. 44B. There may be one trigger 3710 on each side of the device, where a user may require, for example, a thumb and a second finger, to squeeze the triggers 3710 towards one another, in order to fire the applicator assembly 3700. Other embodiments may include additional snap features, for example, up to six snap features, and more than two triggers, for example, three separate triggers.

A further monitor 1700 according to a seventh embodiment is shown in FIGS. 45A to 47. The monitor 1700 is a two-piece monitor, and includes a cradle or base 1710 and a separate transmitter 1720 that is configured to be assembled to the cradle 1710 to form a single functional unit.

The cradle 1710 includes an adhesive layer 1711 which may have an enlarged footprint compared to a main body 1712 of the base 1710. The enlarged adhesive layer 1711 may facilitate a more secure attachment to a patient's body, particularly for continuous glucose monitors that may be attached for multiple days or weeks at a time. The main body 1712 is wedge-shaped to match a substantial wedge shape of the transmitter 1720 described in greater detail below. The cradle 1710 further includes electrical contacts 1713, which may be housed in a raised portion 1714 of the cradle. The contacts may include an elastomeric backing for a flex circuit connection or interface, and/or a durometer may be tuned for contact squeezing. The raised portion 1714 and associated contacts 1713 are at an end of the wedge in the illustrated embodiment, but in other embodiments, may be placed in other positions. The raised portion 1714 may further include other components, for example, a battery to power the entire monitor 1700. The cradle 1710 further includes rails 1715 to guide insertion of the transmitter 1720 to connect to the cradle 1710 in the correct orientation. A flex beam 1716 may further be provided to facilitate secure attachment of the transmitter 1720 to the cradle 1710, as well as to facilitate removal of the transmitter therefrom when either the cradle 1710 or the transmitter 1720, or both, need to be replaced. On the flex beam 1716, there may be a further latch, snap, or other locking feature 1717 to further enhance connection with the transmitter, and perforations 1718 may further be provided, for example, on the adhesive layer 1711, to provide a temporary hold of the flex beam 1716 to the rest of the cradle 1710, while also facilitating easy detachment or tearing away of the flex beam 1716 therefrom during removal. While not shown, the sensor member may further be attached to and extend out of a bottom side of the cradle, and is configured to extend under a patient's skin when the cradle is attached to a surface of the skin. The sensor may be made of or attached to a flex circuit that has gold plated flaps that extend into a silicone backing in the raised portion 1714 of the cradle for robust diametrical contact with the electrical contacts 1713. The electrical contacts 1713 may facilitate electrical communication between the electrodes of the sensor member and the transmitter 1720 when the transmitter 1720 is connected to the cradle 1710.

Figure 46:
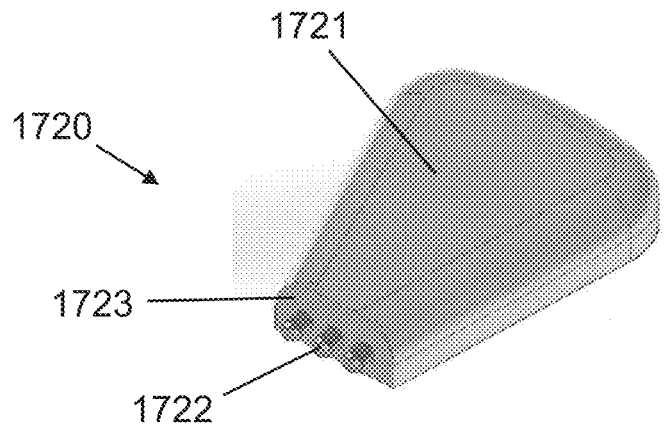
FIG. 46 shows a perspective view of a transmitter of the monitor of the seventh embodiment.
Figure 47:
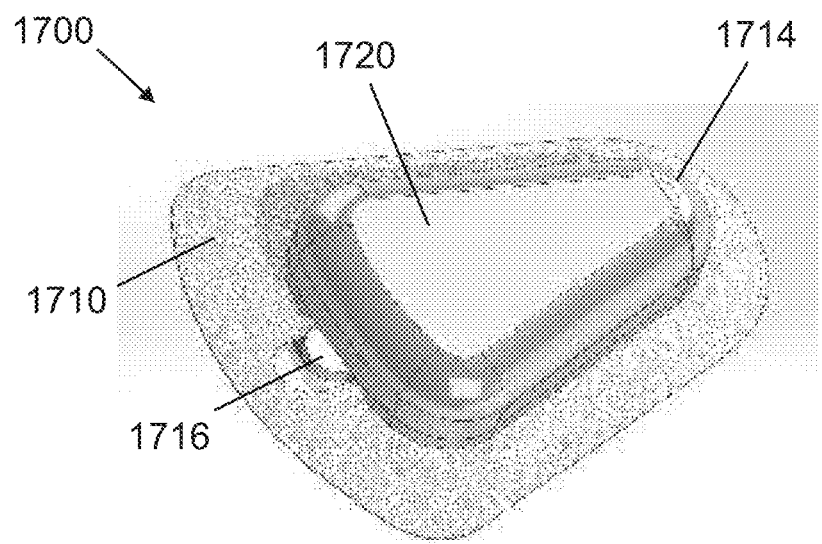
FIG. 47 shows a perspective view of the monitor of the seventh embodiment, with the transmitter shown in FIG. 46 assembled to the cradle shown in FIGS. 45A to 45C.
Figures 48, 49:
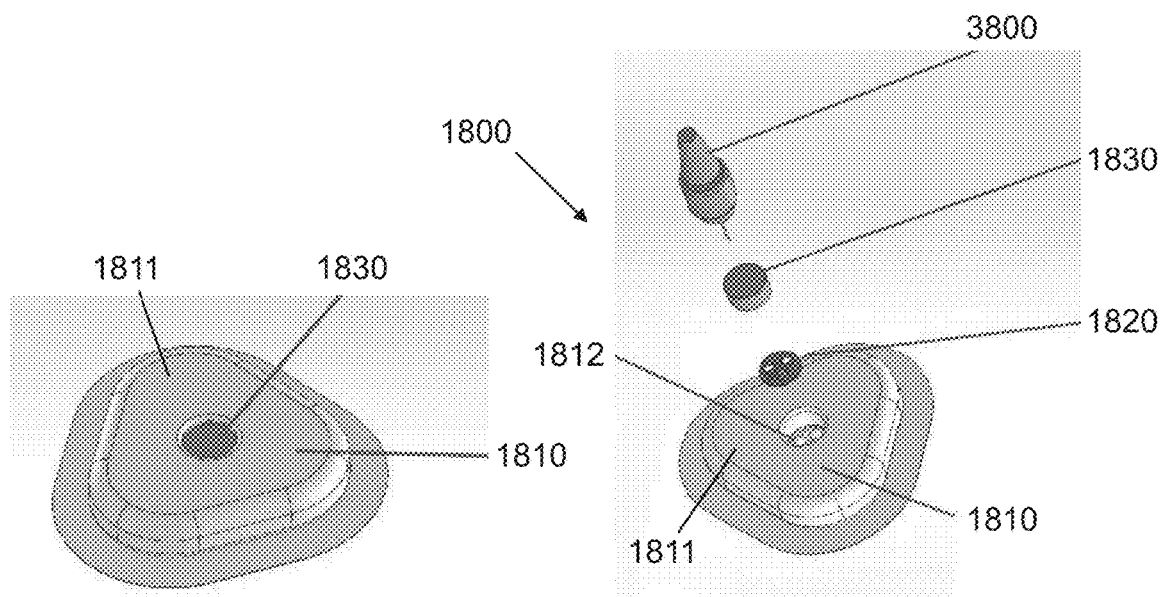
FIG. 48 shows a perspective view of a monitor according to an eighth embodiment.
FIG. 49 shows an exploded perspective view of the monitor of FIG. 48 and a portion of an applicator assembly for the monitor.
Figure 50:
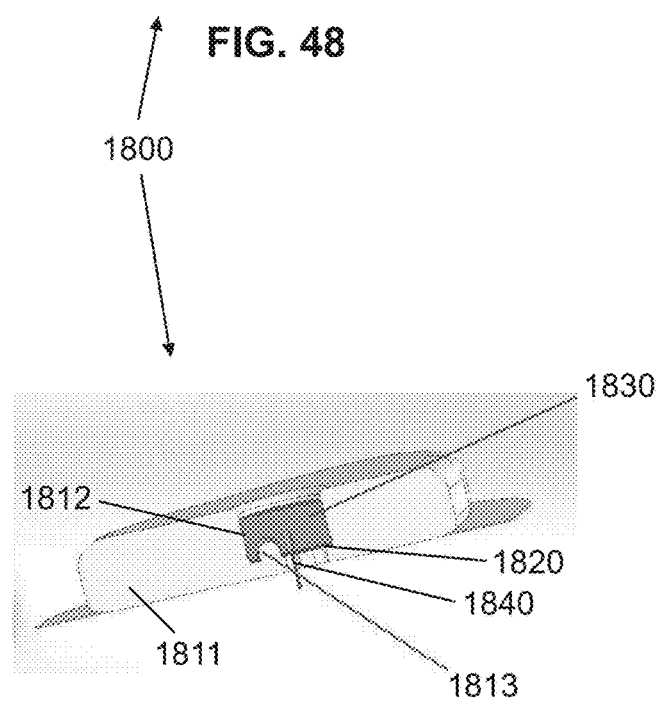
FIG. 50 shows a cross-sectional view of the monitor of FIGS. 48 and 49.
Figure 51:
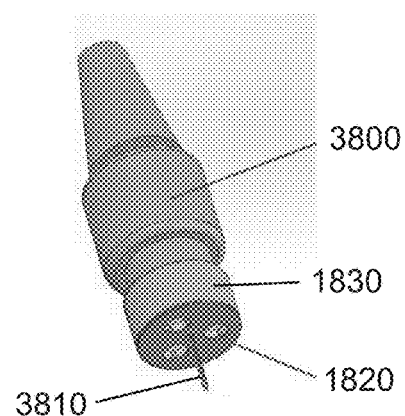
FIG. 51 shows a perspective view of the portion of the applicator assembly shown in FIG. 49 loaded with select components of the monitor of FIGS. 48 to 50.

The transmitter 1720, as shown in FIG. 46, may also be wedge-shaped, and may include a main body 1721 that houses the transmitter, and in some embodiments, a processor, memory, other electronics, and/or a battery. It is to be noted that a battery only needs to be housed in one of the cradle 1710 or the transmitter 1720, so if the cradle 1710 houses a battery, then the transmitter 1720 does not need to house a separate battery, and vice versa. The transmitter further includes fixed electrical contacts 1722 configured to engage with the contacts 1713 of the cradle. The contacts 1722 extend out of a flat end face 1723 of the transmitter that is configured to mate with the raised portion 1714 of the cradle 1710 when the parts are assembled together.

To assemble the transmitter 1720 to the cradle 1710, the transmitter can be placed on the body 1712 of the cradle and can then be slid towards the electrical contacts 1713. During sliding of the transmitter 1720, the rails 1715 ensure proper alignment between the contacts 1713 and 1722 when the connect. Upon assembly of the transmitter 1720 to the cradle 1710, the respective wedge shapes are complementary, and the transmitter 1720 snaps into place on the cradle 1710. When the transmitter 1720 has been fully advanced to its final connected position on the cradle 1710, the catch 1717 may further help hold the transmitter 1720 in proper position relative to the cradle 1710. Due to the positioning of the catch 1717, the transmitter 1720 is allowed to snap into place but is not allowed to disengage after assembly, since the catch 1717 is inaccessible after assembly and while the monitor 1700 is being worn. Thereafter, when removal of the assembly is desired (e.g., when a desired lifespan of either the sensor member, the transmitter 1720, or another component such as an integrated battery has ended), the device is removed from the body, and the flex beam 1716 can then be pulled down from the bottom of the cradle to release the transmitter 1720 from catch 1717 of the cradle 1710. The transmitter 1720 can then easily slide out and be reused with a different cradle 1710. The placement of the flex beam 1716, and the requirement for it to be pulled down under the assembly, prevents inadvertent dislodging of the transmitter 1720, so long as the cradle 1710 remains securely fastened against a user's skin. In addition, pulling of the flex beam 1716 from below the cradle 1710 to release the catch 1717 requires tearing along the perforations 1718, such that the cradle 1710 cannot properly hold the transmitter 1720 again afterwards and must be discarded. This type of design may be advantageous in situations where disconnecting and reconnecting and/or reusing the same cradle 1710 may be undesirable, such as when a battery in the cradle has been depleted and/or when undesired reconnection might allow a user to continue to generate data beyond an approved use period.

Separation of the cradle from the transmitter can provide additional flexibility, for example, for sterilization. The applicator assembly holding the cradle and the sensor assembly may be sterile, while the transmitter can be reusable and does not need to be sterile since no part of the transmitter enters the patient's body.

An eighth embodiment of a monitor 1800 is shown in FIGS. 48 to 51. The monitor 1800 differs from the monitor 1700, in that the monitor 1800 is a disposable continuous glucose monitor, intended to be a one-piece monitor that is removed and discarded in one piece after use. The monitor 1800 includes a main body 1810, a sensor flex circuit 1820, an elastomeric septum 1830, and a sensor member 1840.

The main body 1810 includes an adhesive patch 1811 with an integrated transmitter. At a center of the main body 1810, a recessed portion 1812 includes fixed electrical contacts 1813, where the recessed portion 1812 is configured to house the flex circuit 1820, the elastomeric septum 1830, and at least part of the sensor member 1840. The recessed portion 1812 provides an elastomeric backing for an electrical flex circuit, and/or a tunable hole diameter and durometer for a more robust electrical connection. The main body 1810 can be non-sterile, as no part of the main body 1810 is configured to enter the patient's body.

The sensor flex circuit 1820 is polyimide sterile, and may include gold plated flaps that extend into the elastomeric septum for robust diametrical contact when inserted onto male transmitter contacts, for example, the contacts 1813 provided in the recessed portion 1812 of the main body 1810.

The elastomeric septum 1830 is pierceable and self-sealing. The self-sealing nature of the septum 1830 allows the inserter 3800 to place the sensor member 1840 through the septum 1830 and into the dermis, and self-seals after removal of the inserter 3800, with the sensor member 1840 remaining in place in the monitor assembly and electrically connected to the other portions of the monitor 1800.

The inserter 3800 may be part of a larger applicator assembly, and may include similar features as discussed with respect to prior embodiments. The inserter 3800 may include a needle 3810, which houses and helps advance the sensor member 1840 through the septum 1830 and the flex circuit 1820, and under the patient's skin, and can then be removed axially after the monitor 1800 is fully assembled. In another method of use, the inserter 3800 is assembled with the main body 1810 to assemble all of the respective parts of the monitor 1800 together prior to application onto the patient's skin. Thereafter, the patient actuates the inserter 3800 to apply the entire monitor 1800 onto the patient's skin and simultaneously implant the sensor member 1840 under the patient's skin.

A cradle 1910 of a monitor according to a ninth embodiment is shown in FIGS. 52 to 54B. In this embodiment, a generic snap in cradle 1910 is schematically shown for simplicity, while additional components that would typically be part of a cradle are not shown. The cradle 1910 includes a housing 1920 for the sensor, a hole or bore 1930 that extends through the cradle, a flex circuit 1940, an elastomeric grommet 1950, and a sensor member 1960.

The housing 1920 houses at least part of the sensor member 1960, as well as other components, for example, the flex circuit 1940 and the grommet 1950. The flex circuit 1940 has conductive flaps housed in the elastomeric grommet 1950 for robust electrical connections with fixed male pin terminals on the transmitter (not shown). The elastomeric grommet 1950 seals the penetration site and is tunable, with respect to hole size and/or durometer, for facilitating robust electrical connections.

Figure 52:
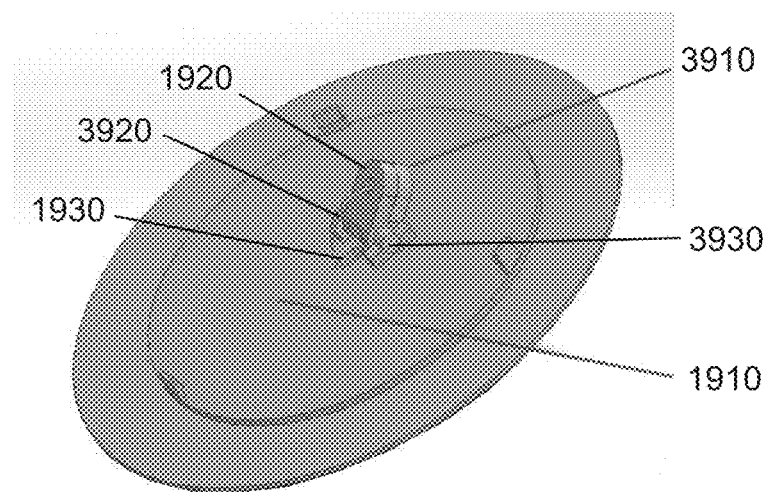
FIG. 52 shows a schematic perspective view of a cradle of a monitor according to a ninth embodiment, with part of an applicator assembly attached thereto before deployment of a needle of the applicator assembly.

In the embodiment shown, the inserter is a rotary inserter, which includes an inserter body 3910, a curved needle 3920, and a hinged or other rotatable connection 3930. FIG. 52 illustrates the rotary inserter 3910 in a ready to deploy position, with the needle 3920 passing through the housing 1920 and holding the sensor member 1960.

Figure 53A:
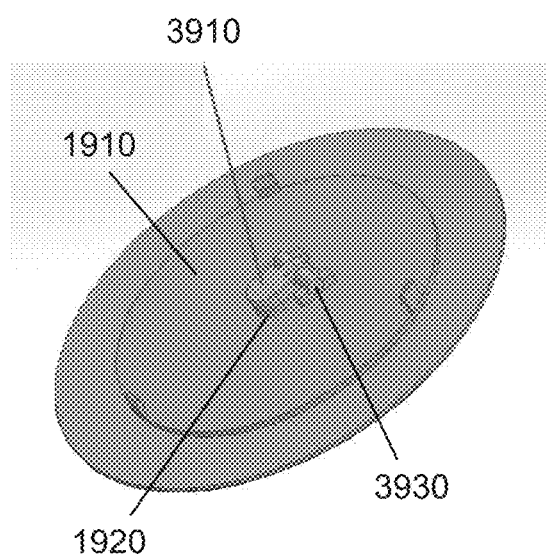
FIG. 53A shows the cradle of the monitor and the part of the applicator assembly shown in FIG. 52, with the needle of the applicator assembly deployed.
Figure 53B:
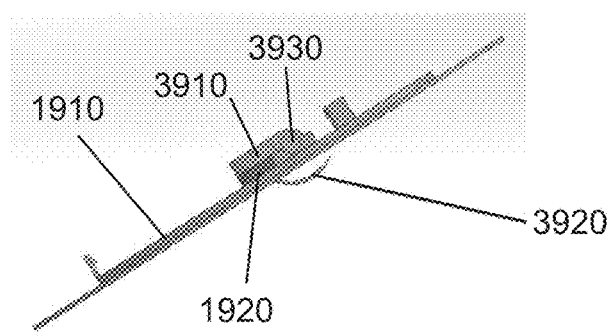
FIG. 53B shows a side view of the cradle of the monitor and the part of the applicator assembly in the state shown in FIG. 53A.

FIGS. 53A and 53B show the rotary inserter 3910 in a deployed position. Upon deployment, the rotary inserter 3910 drives the curved needle 3920 and the curved sensor 1960 into the dermis of the patient. The hinged connection 3930 facilitates a proper rotation of the needle 3920 into the patient's skin. Insertion of the sensor using such a rotary inserter 3910 may allow for more controlled depth of the sensor member 1960, and may resist pullout of the sensor member 1960 better than a traditional linear insertion. Such insertion may also prevent unintended penetration deeper into the interstitial fluid if deeper insertion of the sensor member 1960 is not desired.

Figure 54A:
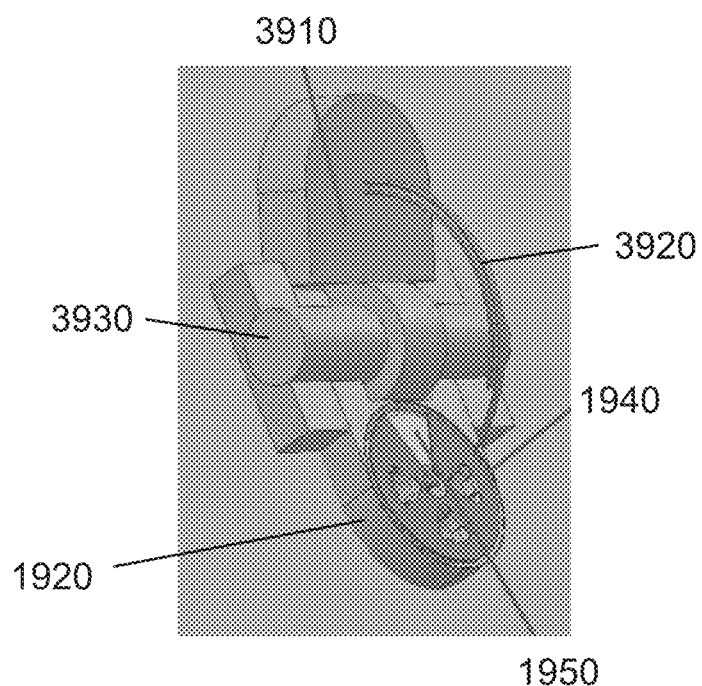
FIG. 54A shows a close-up perspective view of the part of the applicator assembly shown in FIGS. 52 to 53B, after the needle of the applicator assembly has been retracted.
Figure 54B:
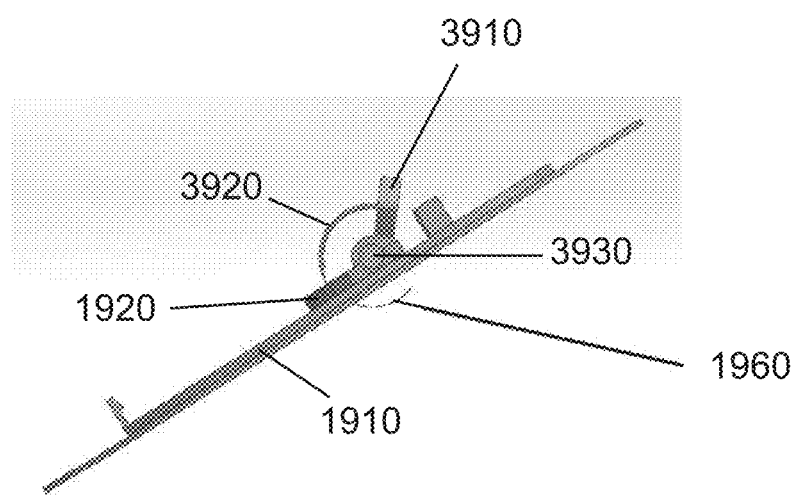
FIG. 54B shows a side view of the part of the applicator assembly in the state shown in FIG. 54A, together with the cradle of the monitor.

FIGS. 54A and 54B show the rotary inserter 3910 after retraction of the needle 3920 out of the patient's body, leaving the sensor member 1840 under the patient's skin. Retraction of the curved needle 3920 may simply involve rotating the inserter 3910 back via the hinge 3930. After retraction, different means of removing the inserter 3910 from the cradle 1910 may be implemented to allow for safe capture of the needle 3920. For example, the hinge 3930 of the rotary inserter 3910 may be unmateable or otherwise releasable from the cradle assembly 1910, whereby a user can then safely capture the needle 3920 in a separate sharps guard.

In addition to the embodiments that have already been described above, it is also possible to combine embodiments, e.g., different features from the various described embodiments, to provide even more different variations of applicator assemblies and/or monitors, without departing from the spirit or scope of the invention. In addition, the inventions should not be limited to the structures and/or shapes described in the embodiments above.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present disclosure, and should not be interpreted in an idealized or overly formal sense, unless expressly so defined herein.

While the subject matter of the present disclosure has been described in connection with certain embodiments, it is to be understood that the subject matter of the present disclosure is not limited to the disclosed embodiments, but, on the contrary, the present disclosure is intended to cover various modifications and equivalent arrangements included within the spirit and scope of the appended claims, and equivalents thereof.

What is claimed is:

1. An applicator assembly for applying at least a portion of an analyte monitor, the applicator assembly comprising:
    a frame having a first end, a second end, a longitudinal axis extending between the first and second ends, and an opening at the second end;
    a resilient member positioned at least partially in the frame and having at least a first portion fixed relative to the frame and a second portion movable relative to the frame in a direction substantially parallel to the longitudinal axis;
    a needle movable together with the second portion of the resilient member; and
    a cap engageable with the frame to cover at least part of the opening;
    wherein when the cap is connected to the frame at a first configuration, the second portion of the resilient member is at a first axial position relative to the frame, and the cap is restricted from separating from the frame;
    wherein the cap is adjustable from the first configuration to a second configuration to increase a bias on the resilient member and to move the second portion of the resilient member to a second axial position relative to the frame that is farther from the opening;
    wherein when the cap is at the second configuration, the cap is separable from the frame, while the second portion of the resilient member is configured to be held at the second axial position relative to the frame; and
    wherein the hold on the second portion of the resilient member is releasable, such that the bias on the resilient member advances the second portion of the resilient member and the needle towards the opening to a position where at least a tip of the needle extends axially out of the opening.

2. The applicator assembly of claim 1, wherein the analyte monitor is a continuous glucose monitor.

3. The applicator assembly of claim 1, wherein the at least a portion of the analyte monitor comprises a sensor member of the analyte monitor.

4. The applicator assembly of claim 3, wherein a separate transmitter is connectable to the sensor member after the sensor member is applied by the applicator assembly.

5. The applicator assembly of claim 1, wherein the second end of the frame defines the opening and extends substantially along a first plane, and wherein the longitudinal axis of the frame forms an acute angle with the first plane.

6. The applicator assembly of claim 5, wherein the acute angle formed between the longitudinal axis of the frame and the first plane is approximately 40°.

7. The applicator assembly of claim 5, wherein a concave channel that extends away from the first plane is formed in the second end of the frame.

8. The applicator assembly of claim 1, wherein the resilient member further comprises a spring portion.

9. The applicator assembly of claim 8, wherein the spring portion is integrally formed with the first and second portions of the resilient member.

10. The applicator assembly of claim 8, wherein when the cap is adjusted from the first configuration to the second configuration, the cap is configured to directly increase the bias on the spring portion.

11. The applicator assembly of claim 10, wherein the cap comprises at least one ramp configured to directly engage the resilient member for biasing the spring portion.

12. The applicator assembly of claim 1, wherein the cap is rotatable relative to the frame to adjust the cap from the first configuration to the second configuration.

13. The applicator assembly of claim 12, wherein the cap is restricted from being separated axially from the frame when the cap is at the first configuration, and wherein the cap is separable axially from the frame when the cap is at the second configuration.

14. The applicator assembly of claim 1, wherein when the needle is advanced to the position where at least the tip of the needle extends axially out of the opening, a stop prevents further movement of the needle out of the opening.

15. The applicator assembly of claim 14, wherein when the stop prevents further movement of the needle out of the opening, at least part of the second portion of the resilient member is configured to move axially past the needle out of the opening to a position where the needle is covered by the second portion of the resilient member.

16. The applicator assembly of claim 14, wherein when the needle reaches the stop, the needle is configured to move back in a direction opposite the direction of advancement and away from the opening to a position where the needle is covered by the second portion of the resilient member.

17. The applicator assembly of claim 1, wherein the needle is held by a needle holder that is movable independently from the resilient member, wherein when the needle is advanced to the position where at least the tip of the needle extends axially out of the opening, the needle holder comprises a resilient portion configured to move the needle in a direction opposite the direction of advancement and away from the opening.

18. A kit comprising the applicator assembly of claim 1 and at least a sensor member of the analyte monitor, wherein the needle comprises a slot that forms a longitudinal opening extending along a length of the needle, and wherein the sensor member is positionable in the slot.

19. The kit of claim 18, wherein the sensor member comprises an end having a first width and a neck portion having a second width less than the first width, and wherein a width of the longitudinal opening on the needle is less than the first width and greater than the second width.

20. The kit of claim 18, wherein the sensor member comprises a first engagement portion engageable with a second engagement portion of the needle, such that when the needle is advanced towards the opening of the frame, the first and second engagement portions engage to pull the sensor member together with the needle towards the opening of the frame, while the first and second engagement portions are configured to release when the needle is retracted away from the opening of the frame.

\* \* \* \* \*